(12) United States Patent
Sedrani et al.

(10) Patent No.: US 8,362,040 B2
(45) Date of Patent: Jan. 29, 2013

(54) 4-PHENYLPIPERIDINE DERIVATIVES AS RENIN INHIBITORS

(75) Inventors: Richard Sedrani, Basel (CH); Juergen Klaus Maibaum, Weil-Haltingen (DE); Werner Breitenstein, Basel (CH); Holger Sellner, Therwil (CH); Claus Ehrhardt, Lorrach (DE); Nils Ostermann, Binzen (DE)

(73) Assignee: Novartis AG, Basel (CH)

( * ) Notice: Subject to any disclaimer, the term of this patent is extended or adjusted under 35 U.S.C. 154(b) by 210 days.

(21) Appl. No.: 12/789,892

(22) Filed: May 28, 2010

(65) Prior Publication Data

US 2010/0240679 A1    Sep. 23, 2010

Related U.S. Application Data

(60) Division of application No. 12/163,038, filed on Jun. 27, 2008, now Pat. No. 7,754,727, which is a continuation of application No. 10/580,296, filed as application No. PCT/EP2004/013410 on Nov. 25, 2004, now abandoned.

(60) Provisional application No. 60/525,375, filed on Nov. 26, 2003.

(51) Int. Cl.
*A01N 43/40* (2006.01)
*A61K 31/445* (2006.01)
*C07D 211/40* (2006.01)
*C07D 211/54* (2006.01)

(52) U.S. Cl. .................................. 514/327; 546/216

(58) Field of Classification Search ..................... None
See application file for complete search history.

(56) References Cited

U.S. PATENT DOCUMENTS

| | | | |
|---|---|---|---|
| 6,051,712 A | 4/2000 | Binggeli et al. | |
| 6,150,526 A | 11/2000 | Binggeli et al. | |
| 6,197,959 B1 | 3/2001 | Breu et al. | |
| 6,376,672 B1 | 4/2002 | Breu et al. | |
| 7,754,727 B2 * | 7/2010 | Sedrani et al. ............... 514/256 | |
| 2002/0087002 A1 | 7/2002 | Breu et al. | |
| 2004/0204455 A1 | 10/2004 | Cody et al. | |

FOREIGN PATENT DOCUMENTS

| | | |
|---|---|---|
| WO | 97/09311 A1 | 3/1997 |
| WO | 00/63173 A1 | 10/2000 |
| WO | 02/076440 A2 | 10/2002 |
| WO | WO02/076440    * | 10/2002 |
| WO | 02/088101 A2 | 11/2002 |
| WO | 2004/089915 A1 | 10/2004 |

OTHER PUBLICATIONS

Bursavich, et. al. Organic Letters, (2001) 3(17), 2625-2628.*
Bursavich, et al., "Solid-Phase Synthesis of Aspartic Peptidase Inhibitors: 3-Alkoxy-4-Aryl Piperidines", Organic Letters, 2001, vol. 3, No. 17, pp. 2625-2628.

* cited by examiner

*Primary Examiner* — Jeffrey Murray
(74) *Attorney, Agent, or Firm* — Sophie Binet Cross

(57) ABSTRACT

Compounds of the present invention having the formula

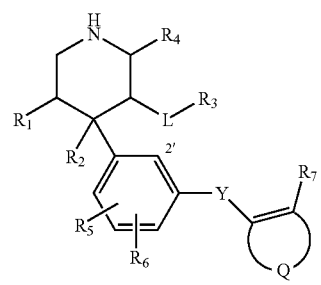

(I)

exhibit inhibitory activity on the natural enzyme renin. Thus, compounds of formula (I) may be employed for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

11 Claims, No Drawings

4-PHENYLPIPERIDINE DERIVATIVES AS RENIN INHIBITORS

This application is a divisional application of U.S. application Ser. No. 12/163,038 filed Jun. 27, 2008, which is a continuation of U.S. application Ser. No. 10/580/296, filed Jul. 21, 2006, which claims benefit of U.S. Provisional Application 60/525,375, filed Nov. 26, 2003.

The present invention provides compounds of the formula

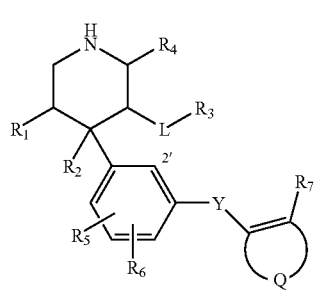

(I)

wherein
$R_1$ is —$CH_2$—X, —O—X or —$S(O)_{0-2}$—X; or
$R_1$ is —$NR_8$—X, —$NR_8C(O)$—X or —$NR_8S(O)_2$—X in which
 $R_8$ is hydrogen or lower alkyl; and
X is —$(CH_2)_m$—$(CR_9R_{10})_p$—$(CH_2)_n$—Z—$(CH_2)_q$—W in which
 m, n and q are independently zero or an integer from 1 to 5;
 p is zero or 1;
 $R_9$ and $R_{10}$ are independently hydrogen, hydroxy, halogen, lower alkyl, lower alkoxy or cycloalkyl; or
 $R_9$ and $R_{10}$ combined are alkylene which together with the carbon atom to which they are attached form a 3- to 6-membered ring;
 Z is a bond; or
 Z is O, $S(O)_{0-2}$, or —$NR_{11}$— in which
  $R_{11}$ is hydrogen or lower alkyl, provided that $R_1$ is —$CH_2$—X when m, n and p are all zero;
 W is aryl or heterocyclyl;
$R_2$ is hydrogen, halogen, cyano, hydroxy or lower alkoxy;
L is a bond; or
L is —$(CH_2)_sO$—$(CH_2)_v$— in which
 s and v are independently zero or an integer from 1 to 3; or
L is —C(O)—, —O(O)O—, —OC(O)—, —OC(O)$NR_{12}$—, —$NR_{12}C(O)$—, —$NR_{13}C(O)O$— or —$NR_{13}C(O)NR_{12}$— in which
 $R_{12}$ and $R_{13}$ are independently hydrogen or lower alkyl;
$R_3$ is hydrogen, hydroxy, halogen or cyano provided that L is a bond; or
$R_3$ is optionally substituted lower alkyl, aralkyl, heteroaralkyl, aryl or heterocyclyl; or
$R_3$ and $R_{12}$ combined are alkylene which together with the nitrogen atom to which they are attached form a 5- to 6-membered ring;
$R_4$ is hydrogen, optionally substituted lower alkyl or aryl;
$R_5$ and $R_6$ are independently hydrogen, halogen, hydroxy, trifluoromethyl, optionally substituted lower alkyl, lower alkoxy or cycloalkyl; or
$R_5$ and $R_6$ combined together with the carbon atoms to which they are attached form a fused 5- to 6-membered aromatic or heteroaromatic ring provided that $R_5$ and $R_6$ are attached to carbon atoms adjacent to each other; or
$R_5$ and $R_6$ combined are alkylene which together with the carbon atoms to which they are attached form a fused 5- to 7-membered ring provided that $R_5$ and $R_6$ are attached to carbon atoms adjacent to each other, or
C—$R_5$ and C—$R_6$ may be replaced with nitrogen;
$R_7$ is hydrogen, halogen, hydroxy, trifluoromethyl, optionally substituted lower alkyl, lower alkoxy, cycloalkyl, alkanoyl, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, carboxy, alkoxycarbonyl, aryl, alkenyl, alkynyl, aralkoxy, heterocyclyl including indolyl, imidazolyl, furyl, thienyl, thiazolyl, pyrrolidyl, pyridyl, pyrimidyl, piperidyl, morpholinyl and tetrazolyl; or
$R_7$ and $R_6$ combined are O, $S(O)_{0-2}$, —$NR_{14}$—, —$(CH_2)_{1-2}$—, —O—$CH_2$—, —$CH_2$—O—, —$S(O)_{0-2}$—$CH_2$—, —$CH_2$—$S(O)_{0-2}$—, —$NR_{14}$—$CH_2$—, —$CH_2$—$NR_{14}$—, —$S(O)_{0-2}$—$NR_{14}$— or —$NR_{14}$—$S(O)_{0-2}$— in which
 $R_{14}$ is hydrogen or lower alkyl, provided $R_6$ is located at the 2' position; or
C—$R_7$ may be replaced with nitrogen;
Y is —$(CH_2)_r$—, —O—$(CH_2)_r$—, —$(CH_2)_r$—O—, —$S_{0-2}$—$(CH_2)_r$— or —$(CH_2)_r$—$S_{0-2}$— in which
 r is zero or an integer from 1 to 3;
Q combined with the atoms to which it is attached form a 5- to 6-membered monocyclic aromatic or heteroaromatic ring; or
Q combined with the atoms to which it is attached form a 7- to 12-membered bicyclic aromatic or heterocyclic ring;
or a pharmaceutically acceptable salt thereof.

The compounds of the present invention exhibit inhibitory activity on the natural enzyme renin. Thus, compounds of formula (I) may be employed for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

Listed below are definitions of various terms used to describe the compounds of the present invention. These definitions apply to the terms as they are used throughout the specification unless they are otherwise limited in specific instances either individually or as part of a larger group.

The term "optionally substituted alkyl" refers to unsubstituted or substituted straight- or branched-chain hydrocarbon groups having 1-20 carbon atoms, preferably 1-7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, cycloalkyl, alkanoyl, alkoxy, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, carboxy, alkoxycarbonyl, aryl, alkenyl, alkynyl, aralkoxy, guanidino, heterocyclyl including indolyl, imidazolyl, furyl, thienyl, thiazolyl, pyrrolidyl, pyridyl, pyrimidyl, piperidyl, morpholinyl and the like.

The term "lower alkyl" refers to those optionally substituted alkyl groups as described above having 1-7, preferably 1-4 carbon atoms.

The term "halogen" or "halo" refers to fluorine, chlorine, bromine and iodine.

The term "alkenyl" refers to any of the above alkyl groups having at least two carbon atoms and further containing a carbon to carbon double bond at the point of attachment. Groups having 2-4 carbon atoms are preferred.

The term "alkynyl" refers to any of the above alkyl groups having at least two carbon atoms and further containing a carbon to carbon triple bond at the point of attachment. Groups having 2-4 carbon atoms are preferred.

The term "alkylene" refers to a straight-chain bridge of 2-5 carbon atoms connected by single bonds, e.g., —$(CH_2)_x$—, wherein x is 2 to 5, which may be interrupted with one or more heteroatoms selected from O, $S(O)_{0-2}$ or —NR—, wherein R may be hydrogen, alkyl, cycloalkyl, aryl, acyl, carbamoyl, sulfonyl, sulfamoyl, alkoxycarbonyl, aryloxycarbonyl or aralkoxycarbonyl, or the alkylene may be substituted with one or more substituents selected from alkyl, cycloalkyl, oxo, halogen, hydroxy, carboxy; alkoxy, alkoxycarbonyl and the like.

The term "cycloalkyl" refers to optionally substituted monocyclic, bicyclic or tricyclic hydrocarbon groups of 3-12 carbon atoms, each of which may be substituted by one or more substituents, such as alkyl, halo, oxo, hydroxy, alkoxy, alkanoyl, acylamino, carbamoyl, alkylamino, dialkylamino, thiol, alkylthio, nitro, cyano, carboxy, alkoxycarbonyl, sulfonyl, sulfonamido, sulfamoyl, heterocyclyl and the like.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.

The term "alkanoyl" refers to alkyl-C(O)—.

The term "alkanoyloxy" refers to alkyl-C(O)—O—.

The terms "alkylamino" and "dialkylamino" refer to alkyl-NH— and $(alkyl)_2N$—, respectively.

The term "alkanoylamino" refers to alkyl-C(O)—NH—.

The term "alkylthio" refers to alkyl-S—.

The term "alkylaminothiocarbonyl" refers to alkyl-NHC(S)—.

The term "trialkylsily" refers to $(alkyl)_3Si$—.

The term "trialkylsilyloxy" refers to $(alkyl)_3SiO$—.

The term "alkylthiono" refers to alkyl-S(O)—.

The term "alkylsulfonyl" refers to alkyl-$S(O)_2$—.

The term "alkoxycarbonyl" refers to alkyl-O—C(O)—.

The term "alkoxycarbonyloxy" refers to alkyl-O—C(O)O—.

The term "carbamoyl" refers to $H_2NC(O)$—, alkyl-NHC(O)—, $(alkyl)_2NC(O)$—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.

The term "sulfamoyl" refers to $H_2NS(O)_2$—, alkyl-$NHS(O)_2$—, $(alkyl)_2NS(O)_2$—, aryl-$NHS(O)_2$—, alkyl(aryl)-$NS(O)_2$—, $(aryl)_2NS(O)_2$—, heteroaryl-$NHS(O)_2$—, aralkyl-$NHS(O)_2$—, heteroaralkyl-$NHS(O)_2$— and the like.

The term "sulfonamido" refers to alkyl-$S(O)_2$—NH—, aryl-$S(O)_2$—NH—, aralkyl-$S(O)_2$—NH—, heteroaryl-$S(O)_2$—NH—, heteroaralkyl-$S(O)_2$—NH—, alkyl-$S(O)_2$—N(alkyl)-, aryl-$S(O)_2$—N(alkyl)-, aralkyl-$S(O)_2$—N(alkyl)-, heteroaryl-$S(O)_2$—N(alkyl)-, heteroaralkyl-$S(O)_2$—N(alkyl)- and the like.

The term "sulfonyl" refers to alkylsulfonyl, arylsulfonyl, heteroarylsulfonyl, aralkylsulfonyl, heteroaralkylsulfonyl and the like.

The term "optionally substituted amino" refers to a primary or secondary amino group which may optionally be substituted by a substituent, such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carbamoyl and the like.

The term "aryl" or "aromatic ring" refers to monocyclic or bicyclic aromatic hydrocarbon groups having 6-12 carbon atoms in the ring portion, such as phenyl, biphenyl, naphthyl and tetrahydronaphthyl, each of which may optionally be substituted by 1-4 substituents, such as alkyl, trifluoromethyl, cycloalkyl, halo, hydroxy, alkoxy, acyl, alkanoyloxy, aryloxy, optionally substituted amino, thiol, alkylthio, arylthio, nitro, cyano, carboxy, alkoxycarbonyl, carbamoyl, alkylthiono, sulfonyl, sulfonamido, heterocyclyl and the like.

The term "monocyclic aryl" refers to optionally substituted phenyl as described under aryl.

The term "aralkyl" refers to an aryl group bonded directly through an alkyl group, such as benzyl.

The term "aralkanoyl" refers to aralkyl-C(O)—.

The term "aralkylthio" refers to aralkyl-S—.

The term "aralkoxy" refers to an aryl group bonded directly through an alkoxy group.

The term "arylsulfonyl" refers to aryl-$S(O)_2$.

The term "arylthio" refers to aryl-S—.

The term "aroyl" refers to aryl-C(O)—.

The term "aroyloxy" refers to aryl-C(O)—O—.

The term "aroylamino" refers to aryl-C(O)—NH—.

The term "aryloxycarbonyl" refers to aryl-O—C(O)—.

The term "heterocyclyl", "heterocyclo" or "heterocyclic ring" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl", "heterocyclo" or "heterocyclic ring" includes substituted heterocyclic groups. Substituted heterocyclic groups refer to heterocyclic groups substituted with 1, 2 or 3 substituents selected from the group consisting of the following:
(a) alkyl;
(b) hydroxy (or protected hydroxy);
(c) halo;
(d) oxo, i.e., =O;
(e) optionally substituted amino, alkylamino or dialkylamino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(l) nitro;
(m) cyano;
(n) sulfamoyl or sulfonamido;
(O) aryl;
(p) alkanoyloxy;
(q) aroyloxy;
(r) arylthio;
(s) aryloxy;
(t) alkylthio;
(u) formyl;
(v) carbamoyl; and
(w) aralkyl.

The term "heterocyclooxy" denotes a heterocyclic group bonded through an oxygen bridge.

The term "heteroaryl" or "heteroaromatic ring" refers to an aromatic heterocycle, e.g., monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., lower alkyl, lower alkoxy or halo.

The term "heteroarylsulfonyl" refers to heteroaryl-$S(O)_2$—.

The term "heteroaroyl" refers to heteroaryl-$C(O)$—.

The term "heteroaroylamino" refers to heteroaryl-$C(O)$NH—.

The term "heteroaralkyl" refers to a heteroaryl group bonded through an alkyl group.

The term "heteroaralkanoyl" refers to heteroaralkyl-$C(O)$—.

The term "heteroaralkanoylamino" refers to heteroaralkyl-$C(O)$NH—.

The term "acyl" refers to alkanoyl, aroyl, heteroaroyl, aralkanoyl, heteroaralkanoyl and the like.

The term "acylamino" refers to alkanoylamino, aroylamino, heteroaroylamino, aralkanoylamino, heteroaralkanoylamino and the like.

Pharmaceutically acceptable salts of any compound of the present invention refer to salts formed with acids, namely acid addition salts, such as of mineral acids, organic carboxylic and organic sulfonic acids, e.g., hydrochloric acid, maleic acid and methanesulfonic acid.

Similarly salts formed with bases, namely cationic salts, such as alkali and alkaline earth metal salts, such as sodium, lithium, potassium, calcium, magnesium, as well as ammonium salts, such as ammonium, trimethylammonium, diethylammonium, and tris(hydroxymethyl)methylammonium salts and salts with amino acids, are possible provided an acidic group constitutes part of the structure.

As described herein above, the present invention provides piperidine derivatives of formula (I), pharmaceutical compositions containing them, methods for preparing said compounds, and methods of treating renin mediated conditions by administration of a therapeutically effective amount of a compound of the present invention, or a pharmaceutical composition thereof.

The groups of compounds mentioned below are not to be regarded as exclusive, rather, e.g., in order to replace general definitions with more specific definitions, parts of those groups of compounds can be interchanged or exchanged for the definitions given above, or omitted, as appropriate.

Preferred are compounds of formula (I) wherein
$R_1$ is —$CH_2$—X, —O—X or —$S(O)_{0-2}$—X; or
$R_1$ is —$NR_8$—X, —$NR_8C(O)$—X or —$NR_8S(O)_2$—X in which
  $R_8$ is hydrogen or lower alkyl; and
X is —$(CH_2)_m$—$(CR_9R_{10})_p$—$(CH_2)_n$—Z—$(cH_2)_q$—W in which
  m and n are independently zero or an integer from 1 to 5;
  p is zero or 1;
  q is zero;
  $R_9$ and $R_{10}$ are independently hydrogen, hydroxy, halogen, lower alkyl, lower alkoxy or cycloalkyl; or
  $R_9$ and $R_{10}$ combined are alkylene which together with the carbon atom to which they are attached form a 3- to 6-membered ring;
  Z is a bond; or
  Z is O, $S(O)_{0-2}$, or —$NR_{11}$— in which
    $R_{11}$ is hydrogen or lower alkyl, provided that $R_1$ is —$CH_2$—X when m, n and p are all zero;
  W is aryl or heterocyclyl;
$R_2$ is hydrogen, halogen, cyano, hydroxy or lower alkoxy;
L is a bond; or
L is —$(CH_2)_s$—O—$(CH_2)_v$— in which
  s and v are zero; or
L is —$C(O)$—, —$C(O)O$—, —$OC(O)$—, —$OC(O)NR_{12}$—, —$NR_{13}C(O)$—, —$NR_{13}C(O)O$— or —$NR_{13}C(O)NR_{12}$— in which
  $R_{12}$ and $R_{13}$ are independently hydrogen or lower alkyl;
$R_3$ is hydrogen, halogen or cyano provided that L is a bond; or
$R_3$ is optionally substituted lower alkyl, aralkyl, heteroaralkyl, aryl or heterocyclyl; or
$R_3$ and $R_{12}$ combined are alkylene which together with the nitrogen atom to which they are attached form a 5- to 6-membered ring;
$R_4$ is hydrogen, optionally substituted lower alkyl or aryl;
$R_5$ and $R_B$ are independently hydrogen, halogen, hydroxy, trifluoromethyl, optionally substituted lower alkyl, lower alkoxy or cycloalkyl; or
$R_5$ and $R_6$ combined together with the carbon atoms to which they are attached form a fused 5- to 6-membered aromatic or heteroaromatic ring provided that $R_5$ and $R_6$ are attached to carbon atoms adjacent to each other; or
$R_5$ and $R_6$ combined are alkylene which together with the carbon atoms to which they are attached form a fused 5- to 7-membered ring provided that $R_5$ and $R_6$ are attached to carbon atoms adjacent to each other; or $R_7$ is hydrogen, halogen, hydroxy, trifluoromethyl, optionally substituted, lower alkyl, lower alkoxy or cycloalkyl; or $R_7$ and $R_6$ combined are O, $S(O)_{0-2}$, $-NR_{14}-$, $-(CH_2)_{1-2}-$, $-O-CH_2-$, $-CH_2-O-$, $-S(O)_{0-2}-CH_2-$, $-CH_2-S(O)_{0-2}-$, $-NR_{14}-CH_2-$, $-CH_2-NR_{14}-$, $-S(O)_{0-2}-NR_{14}-$ or $-NR_{14}-S(O)_{0-2}-$ in which $R_{14}$ is hydrogen or lower alkyl, provided $R_6$ is located at the 2' position;

Y is $-(CH_2)_r-$ in which r is zero;

Q combined with the carbon atoms to which it is attached form a 5- to 6-membered monocyclic aromatic or heteroaromatic ring; or Q combined with the carbon atoms to which it is attached form a 9- to 10-membered bicyclic aromatic or heterocyclic ring;

or a pharmaceutically acceptable salt thereof.

Further preferred are compounds of formula (I) having the formula

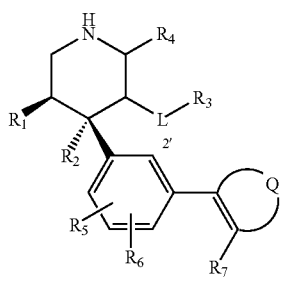

(IA)

wherein $R_1$, $R_2$, L, $R_3$, $R_4$, $R_5$, $R_6$, $R_7$ and Q have meanings as defined herein above;

or a pharmaceutically acceptable salt thereof.

Further preferred are also the compounds of formula (I) having the formula

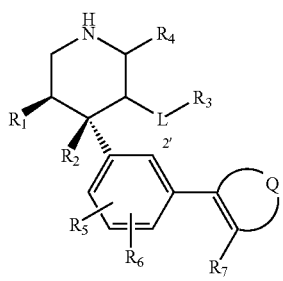

(IB)

wherein $R_1$, $R_2$, L, $R_3$, $R_4$, $R_5$, $R_6$, $R_7$ and Q have meanings as defined herein above;

or a pharmaceutically acceptable salt thereof.

Preferred are compounds of formula (IB), designated as the A group, wherein $R_1$ is $-CH_2-X$, $-O-X$ or $-S-X$; or $R_1$ is $-NR_8-X$, $-NR_8C(O)-X$ or $-NR_8S(O)_2-X$ in which $R_8$ is hydrogen or lower alkyl; and X is $-(CH_2)_m-(CR_9R_{10})_p-(CH_2)_n-Z-W$ in which m and n are independently zero or an integer of 1 or 2;

p is zero or 1;

$R_9$ and $R_{10}$ are independently hydrogen, hydroxy, halogen, lower alkyl, lower alkoxy or cycloalkyl; or $R_9$ and $R_{10}$ combined are alkylene which together with the carbon atom to which they are attached form a 3- to 6-membered ring;

Z is a bond; or

Z is O, $S(O)_{8-2}$, or $-NR_{11}-$ in which $R_{11}$ is hydrogen or lower alkyl, provided that $R_1$ is $-CH_2-X$ when m, n and p are all zero;

W is aryl or heterocyclyl;

$R_2$ is hydrogen, halogen or hydroxy;

L is a bond;

$R_3$ is hydrogen or halogen;

$R_4$ is hydrogen, optionally substituted lower alkyl or aryl;

$R_5$ and $R_6$ are independently hydrogen, halogen, hydroxy, trifluoromethyl, optionally substituted lower alkyl, lower alkoxy or cycloalkyl;

$R_7$ is hydrogen, halogen, hydroxy, trifluoromethyl, optionally substituted lower alkyl, lower alkoxy or cycloalkyl; or $R_7$ and $R_6$ combined are O, $S(O)_{0-2}$, $-NR_{14}-$, $-(CH_2)_{1-2}-$, $-O-CH_2-$, $-CH_2-O-$, $-S(O)_{0-2}-CH_2-$, $-CH_2-S(O)_{0-2}-$, $-NR_{14}-CH_2-$, $-CH_2-NR_{14}-$, $-S(O)_{0-2}-NR_{14}-$ or $-NR_{14}-S(O)_{0-2}-$ in which $R_{14}$ is hydrogen or lower alkyl, provided $R_6$ is located at the 2'-position;

Q combined with the atoms to which it is attached form a 5- to 6-membered monocyclic aromatic or heteroaromatic ring; or Q combined with the atoms to which it is attached form a 9- to 10-membered bicyclic aromatic or heterocyclic ring;

or a pharmaceutically acceptable salt thereof.

Preferred are the compounds in the A group, designated as the B group, wherein $R_1$ is $-CH_2-X$, $-O-X$ or $-S-X$; or $R_1$ is $-NR_8-X$, $-NR_8C(O)-X$ or $-NR_8S(O)_2-X$ in which $R_8$ is hydrogen or lower alkyl; and X is $-(CH_2)_m-(CR_9R_{10})_p-(CF_{12})_n-Z-W$ in which m and n are independently zero or an integer of 1 or 2;

p is zero or 1;

$R_9$ and $R_{10}$ are independently hydrogen or lower alkyl; or

Z is a bond; or

Z is O, $S(O)_{8-2}$, or $-NR_{11}-$ in which $R_{11}$ is hydrogen or lower alkyl, provided that $R_1$ is $-CH_2-X$ when m, n and p are all zero;

W is aryl or heterocyclyl;

$R_2$ is hydrogen, halogen or hydroxy;

L is a bond;

$R_3$ is hydrogen or halogen;

$R_4$ is hydrogen;

$R_5$ and $R_{6e}$ are independently hydrogen, halogen, hydroxy, trifluoromethyl, optionally substituted lower alkyl, lower alkoxy or cycloalkyl;

$R_7$ is hydrogen, halogen, hydroxy, trifluoromethyl, optionally substituted lower alkyl, lower alkoxy or cycloalkyl; or $R_7$ and $R_6$ combined are O, $S(O)_{0-2}$, $-NR_{14}-$, $-(CH_2)_{1-2}-$, $-O-CH_2-$, $-CH_2-O-$, $-S(O)_{0-2}-CH_2-$, $-CH_2-S(O)_{0-2}-$, $-NR_{14}-CH_2-$, $-CH_2-NR_{14}-$, $-S(O)_{0-2}-NR_{14}-$ or $-NR_{14}-S(O)_{0-2}-$ in which
$R_{14}$ is hydrogen or lower alkyl, provided $R_6$ is located at the 2'-position;

Q combined with the atoms to which it is attached form a 5- to 6-membered monocyclic aromatic or heteroaromatic ring; or Q combined with the atoms to which it is attached form a 9- to 10-membered bicyclic aromatic or heterocyclic ring;

or a pharmaceutically acceptable salt thereof.

Preferred are the compounds in the B group wherein
$R_1$ is $-NR_8-X$, $-NR_8C(O)-X$ or $-NR_8S(O)_2-X$ in which
$R_8$ is hydrogen or lower alkyl;

or a pharmaceutically acceptable salt thereof.

Preferred are also the compounds in the B group wherein Q combined with the carbon atoms to which it is attached form a pyridyl or pyrimidinyl ring;

or a pharmaceutically acceptable salt thereof.

Preferred are also the compounds in the B group wherein Q combined with the carbon atoms to which it is attached form a thienyl, furyl, pyrrolyl or indolyl ring;

or a pharmaceutically acceptable salt thereof.

Preferred are also the compounds in the A group, designated as the C group, having the formula

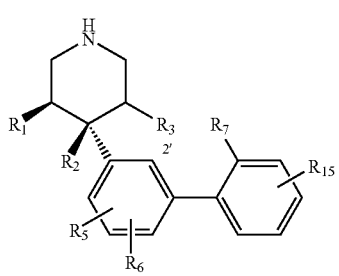

(IC)

wherein
$R_1$ is $-CH_2-X$, $-O-X$ or $-S-X$; or
$R_1$ is $-NR_8-X$, $-NR_8C(O)-X$ or $-NR_8S(O)_2-X$ in which
$R_8$ is hydrogen or lower alkyl; and
X is $-(CH_2)_m-(CR_9R_{10})_p-(CH_2)_n-Z-W$ in which
m, n and p are independently zero or 1;
$R_9$ is hydrogen;
$R_{10}$ is hydrogen or lower alkyl;
Z is a bond; or
Z is O, $S(O)_{0-2}$, or $-NR_{11}-$ in which
$R_{11}$ is hydrogen or lower alkyl, provided that $R_1$ is $-CH_2-X$ when m, n and p are all zero;
W is aryl or heterocyclyl;
$R_2$ is hydrogen;
$R_3$ is hydrogen or halogen;
$R_5$ and $R_6$ are independently hydrogen, halogen, hydroxy, trifluoromethyl, optionally substituted lower alkyl, lower alkoxy or cycloalkyl;
$R_7$ is hydrogen, halogen, hydroxy, trifluoromethyl, optionally substituted lower alkyl, lower alkoxy or cycloalkyl; or $R_7$ and $R_6$ combined are O, $S(O)_{0-2}$, $-NR_{14}-$, $-(CH_2)_{1-2}-$, $-O-CH_2-$, $-CH_2-O-$, $-S(O)_{0-2}-CH_2-$, $-CH_2-S(O)_{0-2}-$, $-NR_{14}-CH_2-$, $-CH_2-NR_{14}-$, $-S(O)_{0-2}-NR_{14}-$ or $-NR_{14}-S(O)_{0-2}-$ in which
$R_{14}$ is hydrogen or lower alkyl, provided $R_6$ is located at the 2'-position;
$R_{15}$ is hydrogen, halogen, hydroxy, trifluoromethyl, optionally substituted lower alkyl, lower alkoxy or cycloalkyl;

or a pharmaceutically acceptable salt thereof.

Preferred are the compounds in the C group wherein
$R_1$ is $-O-X$ or $-S-X$; and
X is $-(CH_2)_m-(CR_9R_{10})_p-(CH_2)_n-Z-W$ in which
m is 1;
n and p are zero;
Z is a bond;
W is aryl or heterocyclyl;
$R_3$ is hydrogen or halogen;
$R_5$ is hydrogen, halogen, hydroxy, trifluoromethyl, optionally substituted lower alkyl, lower alkoxy or cycloalkyl;
$R_6$ is hydrogen;
$R_7$ is hydrogen;
$R_{15}$ is hydrogen, halogen, hydroxy, trifluoromethyl, optionally substituted lower alkyl, lower alkoxy or cycloalkyl;

or a pharmaceutically acceptable salt thereof.

Further preferred are the compounds in the C group wherein
$R_3$ is hydrogen;

or a pharmaceutically acceptable salt thereof.

More preferred are the compounds in the C group wherein
W is monocyclic aryl;

or a pharmaceutically acceptable salt thereof.

Preferred are also the compounds in the A group, designated as the D group, wherein
p is 1;
$R_9$ and $R_{10}$ combined are alkylene which together with the carbon atom to which they are attached form a 3- to 6-membered ring;

or a pharmaceutically acceptable salt thereof.

Preferred are the compounds in the D group having the formula

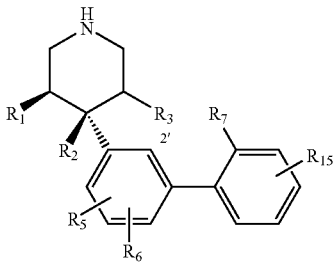

(IC)

wherein
$R_1$ is $-CH_2-X$, $-O-X$ or $-S-X$; or
$R_1$ is $-NR_8-X$, $-NR_8C(O)-X$ or $-NR_8S(O)_2-X$ in which
$R_8$ is hydrogen or lower alkyl; and
X is $-(CH_2)_m-CR_9R_{10}-(CH_2)_n-Z-W$ in which
m and n are 1;
Z is a bond; or
Z is O, $S(O)_{0-2}$, or $-NR_{11}-$ in which
$R_{11}$ is hydrogen or lower alkyl, provided that $R_1$ is $-CH_2-X$ when m, n and p are all zero;
W is aryl or heterocyclyl;

R$_2$ is hydrogen;
R$_3$ is hydrogen or halogen;
R$_5$ and R$_6$ are independently hydrogen, halogen, hydroxy, trifluoromethyl, optionally substituted lower alkyl, lower alkoxy or cycloalkyl;
R$_7$ is hydrogen, halogen, hydroxy, trifluoromethyl, optionally substituted lower alkyl, lower alkoxy or cycloalkyl; or
R$_7$ and R$_8$ combined are O, S(O)$_{0-2}$, —NR$_{14}$—, —(CH$_2$)$_{1-2}$—, —O—CH$_2$—, —CH$_2$—O—, —S(O)$_{0-2}$—CH$_2$—, —CH$_2$—S(O)$_{0-2}$—, —NR$_{14}$—CH$_2$—, —CH$_2$—NR$_{14}$—, —S(O)$_{0-2}$—NR$_{14}$— or —NR$_{14}$—S(O)$_{0-2}$— in which
R$_{14}$ is hydrogen or lower alkyl, provided R$_6$ is located at the 2'-position;
R$_{15}$ is hydrogen, halogen, hydroxy, trifluoromethyl, optionally substituted lower alkyl, lower alkoxy or cycloalkyl;
or a pharmaceutically acceptable salt thereof.

Further preferred are the compounds in the D group wherein
R$_1$ is —O—X or —S—X; and
X is —CH$_2$—CR$_9$R$_{10}$—CH$_2$—Z—W in which
  Z is a bond;
  W is aryl;
R$_3$ is hydrogen;
R$_5$ is hydrogen, halogen, hydroxy, trifluoromethyl, optionally substituted lower alkyl, lower alkoxy or cycloalkyl;
R$_6$ is hydrogen;
R$_7$ is hydrogen;
R$_{15}$ is hydrogen, halogen, hydroxy, trifluoromethyl, optionally substituted lower alkyl, lower alkoxy or cycloalkyl;
or a pharmaceutically acceptable salt thereof.

The compounds of the present invention possess two or more asymmetric centers depending on the choice of the substituents. The preferred absolute configuration at the C-3 and C-4 asymmetric centers is maintained throughout the specification and the appended claims as indicated herein above. However, any possible diastereoisomers, enantiomers and geometric isomers, and mixtures thereof, e.g., racemates, are encompassed by the instant invention.

Particular embodiments of the invention are:
(3R*,4R*)-4-Biphenyl-3-yl-3-(naphthalen-2-ylmethoxy)-piperidine hydrochloride;
(3R*,4R*)-4-Biphenyl-3-yl-3-(biphenyl-4-ylmethoxy)-piperidine hydrochloride;
(3R*,4R*)-3-Benzyloxy-4-biphenyl-3-yl-piperidine hydrochloride;
(3R*,4R*)-4-Biphenyl-3-yl-3-(4-bromo-benzyloxy)-piperidine hydrochloride;
(3R*,4R*)-4-Biphenyl-3-yl-3-(4-trifluoromethoxy-benzyloxy)-piperidine hydrochloride;
(3R*,4R*)-4-Biphenyl-3-yl-3-(3-phenoxy-benzyloxy)-piperidine hydrochloride;
(3R*,4R*)-4-Dibenzofuran-4-yl-3-(naphthalen-2-ylmethoxy)-piperidine hydrochloride;
(3R*,4R*)-3-(Biphenyl-4-ylmethoxy)-4-dibenzofuran-4-yl-piperidine hydrochloride;
(3R*,4R*)-3-Benzyloxy-4-dibenzofuran-4-yl-piperidine hydrochloride;
(3R*,4R*)-4-Dibenzofuran-4-yl-3-(3-phenoxy-benzyloxy)-piperidine hydrochloride;
[3-((3R*,4R*)-4-Dibenzofuran-4-yl-piperidin-3-yloxymethyl)-phenyl]-phenyl-methanone hydrochloride;
(3R*,4R*)-4-(4'-Methoxy-biphenyl-3-yl)-3-(naphthalen-2-ylmethoxy)-piperidine hydrochloride;
3'-[(3R*,4R*)-3-(Naphthalen-2-ylmethoxy)-piperidin-4-yl]-biphenyl-3-ol hydrochloride;
(3R*,4R*)-4-[3'-(2-Methoxy-ethoxy)-biphenyl-3-yl]-3-(naphthalen-2-ylmethoxy)-piperidine hydrochloride;
N-{3'-[(3R*,4R*)-3-(Naphthalen-2-ylmethoxy)-piperidin-4-yl]-biphenyl-3-yl}-acetamide hydrochloride;
1-{3'-[(3R*,4R*)-3-(Naphthalen-2-ylmethoxy)-piperidin-4-yl]-biphenyl-4-yl}-ethanone hydrochloride;
1-{3'-[(3R*,4R*)-3-(Naphthalen-2-ylmethoxy)-piperidin-4-yl]-biphenyl-3-yl}-ethanone hydrochloride;
3'-[(3R*,4R*)-3-(Naphthalen-2-ylmethoxy)-piperidin-4-yl]-biphenyl-3-carboxylic acid ethyl ester hydrochloride;
(3R*,4R*)-4-(3'-Chloro-biphenyl-3-yl)-3-(naphthalen-2-ylmethoxy)-piperidine hydrochloride;
(3R*,4R*)-3-(Naphthalen-2-ylmethoxy)-4-(3'-trifluoromethyl-biphenyl-3-yl)-piperidine hydrochloride;
(3R*,4R*)-4-(4'-Chloro-biphenyl-3-yl)-3-(naphthalen-2-ylmethoxy)-piperidine hydrochloride;
3'-[(3R*,4R*)-3-(Naphthalen-2-ylmethoxy)-piperidin-4-yl]-biphenyl-4-ol hydrochloride;
Dimethyl-{3'-[(3R*,4R*)-3-(Naphthalen-2-ylmethoxy)-piperidin-4-yl]biphenyl-4-yl}-amine hydrochloride;
3'-[(3R*,4R*)-3-(Naphthalen-2-ylmethoxy)-piperidin-4-yl]-biphenyl-3-carboxylic acid hydrochloride;
3'-[(3R*,4R*)-3-(Naphthalen-2-ylmethoxy)-piperidin-4-yl]-biphenyl-4-carboxylic acid methylamide hydrochloride;
4-{3-[(3R*,4R*)-3-(Naphthalen-2-ylmethoxy)-piperidin-4-yl]-phenyl}-pyridine hydrochloride;
(3R*,4R*)-3-(Naphthalen-2-ylmethoxy)-4-(3-thiophen-3-yl-phenyl)-piperidine hydrochloride;
3-{3-[(3R*,4R*)-3-(Naphthalen-2-ylmethoxy)-piperidin-4-yl]-phenyl}-pyridine hydrochloride;
2-{3-[(3R*,4R*)-3-(Naphthalen-2-ylmethoxy)-piperidin-4-yl]-phenyl}-1H-Indole hydrochloride;
5-{3-[(3R*,4R*)-3-(Naphthalen-2-ylmethoxy)-piperidin-4-yl]-phenyl}-pyrimidine hydrochloride;
(3R,4R)-4-Biphenyl-3-yl-3-[2-(3-methoxy-propoxy)-4-methyl-benzyloxy]-piperidine;
(3R,4R)-4-Biphenyl-3-yl-3-[2-(3-methoxy-propoxy)-benzyloxy]piperidine trifluoroacetic acid;
(3R,4R)-4-Biphenyl-3-yl-3-[4-methoxy-3-(-3-methoxy-propoxy)-benzyloxy]-piperidine;
(3R,4R)-4-Biphenyl-3-yl-3-[3-(4-methoxy-butyl)-benzyloxy]-piperidine;
(3R,4R)-4-Biphenyl-3-yl-3-[3-(3-methoxy-propyl)-benzyloxy]-piperidine;
(3R,4R)-4-Biphenyl-3-yl-3-[3-(2-methoxy-ethyl)-benzyloxy]-piperidine;
(3R,4R)-4-Biphenyl-3-yl-3-[3-(3-methoxy-propyl)-4-methyl-benzyloxy]-piperidine;
(3R,4R)-4-Biphenyl-3-yl-3-[3-(4-methoxy-butyl)-4-methyl-benzyloxy]-piperidine;
(3R,4R)-4-Biphenyl-3-yl-3-[2-(3-methoxy-propyl)-benzyloxy]-piperidine trifluoroacetic acid;
(3R,4R)-3-(1-Benzyl-cyclopropylmethyloxy)-4-biphenyl-3-yl-piperidine trifloroacetic acid; and
(3R,4R)-4-Biphenyl-3-yl-3-{1-[2-(3-methoxy-propyl)-benzyl]-cyclopropylmethoxy}-piperidine hydrochloride;
or a pharmaceutically acceptable salt thereof.

Compounds of formula (I) may be prepared from known starting materials according to methods well known in the art, e.g., using methods disclosed in International PCT Patent Application No. WO 97/09311, or as described herein in the illustrative Examples, or modifications thereof.

For example, compounds of formula (IC) having formula (IC') wherein $R_5$, $R_6$, $R_7$, $R_{15}$ have meanings as defined herein above, and $R_1$ is —O—X in which X has a meaning as defined herein above, may be prepared as outlined in Scheme 1.

Scheme 1:

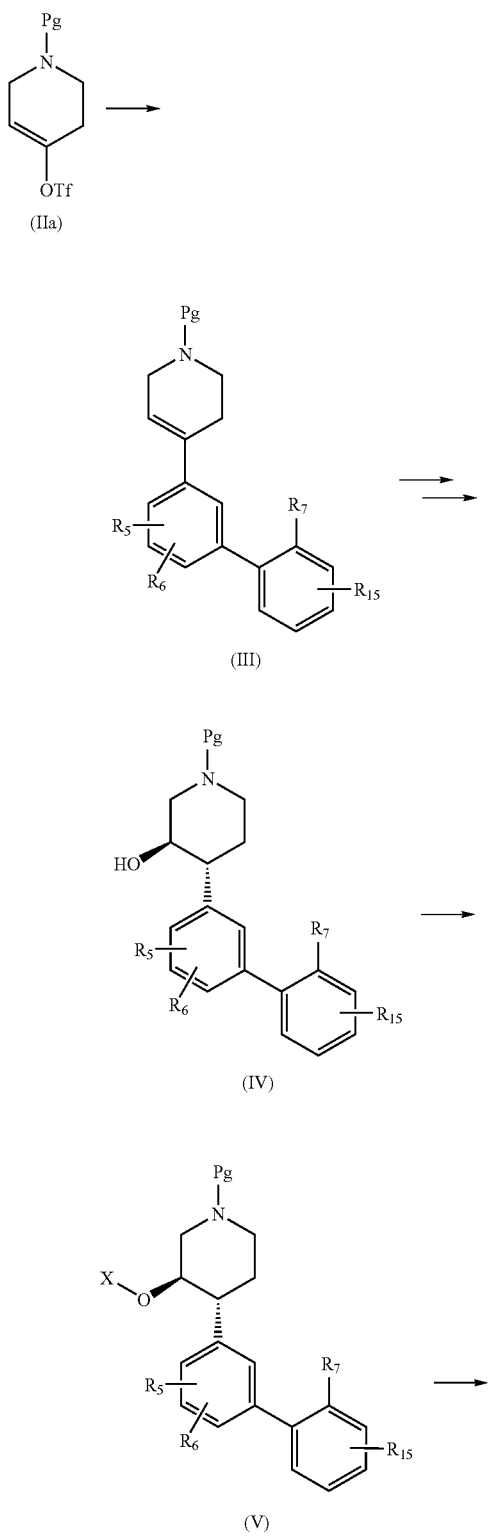

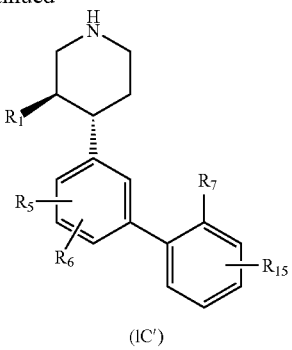

(IC')

Compounds of formula (IIa) wherein Pg represents a protecting group such as a lower alkoxycarbonyl, e.g., t-butoxycarbonyl or ethoxycarbonyl, may be converted to compounds of formula (III) under conditions of Suzuki or Stille coupling, e.g., a compound of formula (IIa) may be reacted with a boronic acid of the formula

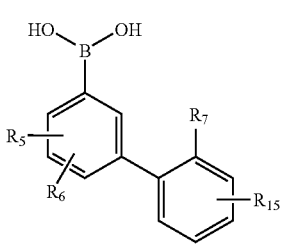

(VI)

wherein $R_5$, $R_6$, $R_7$ and $R_{15}$ have meanings as defined above, in the presence of a palladium catalyst such as tetrakis(triphenylphosphine)palladium(0) and a base such as sodium or potassium carbonate in an appropriate solvent, e.g., water, dimethoxyethane, acetonitrile, methanol, ethanol or THF, or a mixture of solvents thereof. If desired, the Suzuki reaction may be conducted in the presence of an additive such as lithium chloride. Boronic acids of formula (VI) are known, or if they are novel, they may be prepared using to methods known in the art.

A resulting compound of formula (III) may then be hydroxylated under appropriate reaction conditions, e.g., under conditions of hydroboration, to afford a compound of formula (IV) wherein Pg, $R_5$, $R_6$, $R_7$ and $R_{15}$ have meanings as defined above.

A resulting compound of formula (IV) is obtained as a racemic mixture according to the reaction sequence as outlined in Scheme 1. Racemic compounds, e.g., those of formula (IV) and (IC'), may be separated into their pure enantiomers using conventional methods known in the art.

Alternatively, compounds of formula (IV) wherein Pg, $R_5$, $R_6$, $R_7$ and $R_{15}$ have meanings as defined above may be obtained in high enantioselectivity from compounds of formula (III) by a reaction sequence involving asymmetric dihydroxylation followed by catalytic reduction, as described by Rich et al. in *Organic Letters*, 2001, 3, 2317-2320, or as described in International PCT Patent Application No. WO 00/63173.

Compounds of formula (IV) wherein Pg, $R_5$, $R_6$, $R_7$ and $R_{15}$ have meanings as defined above may then be treated, e.g., with an alkylating agent of the formula $$X\text{-}Lg_1 \qquad (VII)$$

wherein X has a meaning as defined herein, and $Lg_1$ represents a leaving group such as iodide, bromide, chloride, trifluoromethylsulfonate, mesylate or tosylate, preferably bromide, in the presence of a base such as sodium hydride in an organic solvent, such as tetrahydrofuran (THF), N,N-dimethylformamide (DMF) or N,N-dimethylacetamide (DMA), to afford compounds of formula (V). Alkylating agents of formula (VII) are known, or if they are novel, they may be prepared as illustrated herein in the Examples, or using methods well known in the art.

Finally, compounds of formula (V) wherein Pg, X, $R_5$, $R_6$, $R_7$ and $R_{15}$ have meanings as defined above may be converted to compounds of formula (IC') wherein $R_5$, $R_6$, $R_7$, $R_{15}$ have meanings as defined herein above, and $R_1$ is —O—X in which X has a meaning as defined herein above, or a pharmaceutically acceptable salt thereof, by removal of the protecting group, e.g., when Pg is t-butoxycarbonyl by treatment with an acid such as trifluoroacetic acid (TFA) or hydrochloric acid (HCl), or when Pg is ethoxycarbonyl by treatment with a base such as aqueous sodium or potassium hydroxide.

Alternatively, compounds of formula (IC') wherein $R_5$, $R_6$, $R_7$, $R_{15}$ have meanings as defined herein above, and $R_1$ is —O—X in which X has a meaning as defined herein above, may be obtained from compounds of formula (IIb) following the reaction sequence as outlined in Scheme 2.

Scheme 2:

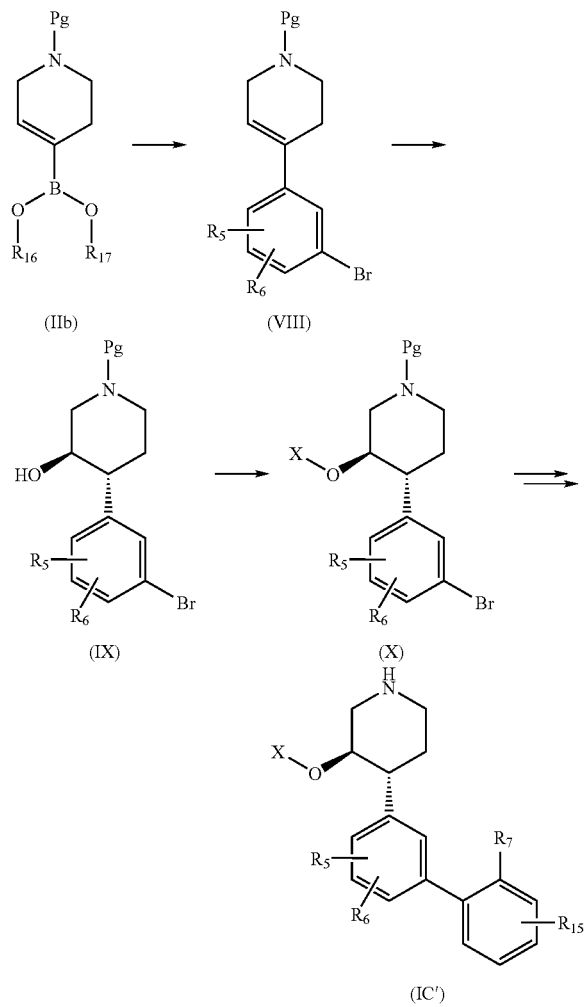

As illustrated in Scheme 2, compounds of formula (IIb) wherein Pg represents a protecting group as described herein above, and $R_{16}$ and $R_{17}$ are lower alkyl, or $R_{16}$ and $R_{17}$ combined are alkylene which together with the boron and the oxygen atoms form a 5- or 6-membered ring, preferably, $R_{16}$ and $R_{17}$ combined are 1,1,2,2-tetramethylethylene, may be converted to compounds of formula (VIII) under conditions of Suzuki coupling, e.g., a compound of formula (IIb) may be treated with a compound of the formula

wherein $R_5$ and $R_6$ have meanings as defined above, in the presence of a palladium catalyst such as tetrakis(triphenylphosphine)palladium(0) and a base such as sodium or potassium carbonate in an appropriate solvent, e.g., water, dimethoxyethane, acetonitrile, methanol, ethanol or THF, or a mixture of solvents thereof. If desired, the Suzuki reaction may be conducted in the presence of an additive such as lithium chloride. Compounds of formulae (IIb) and (XI) are known, or if they are novel, they may be prepared using to methods known in the art.

A resulting compound of formula (VIII) may then be converted to a compound of formula (IX) wherein Pg, $R_5$ and $R_8$ have meanings as defined above, as described herein for compounds of formula (IV).

Compounds of formula (IX) wherein Pg, $R_5$ and $R_6$ have meanings as defined herein above, may then be treated, e.g., with an alkylating agent of formula (VII), to afford compounds of formula (X) wherein Pg, X, $R_5$ and $R_6$ have meanings as defined herein above, under reaction conditions as described herein for compounds of formula (V).

Finally, compounds of formula (X) wherein Pg, X, $R_5$ and $R_6$ have meanings as defined herein above may be converted to compounds of formula (IC') wherein X, $R_5$, $R_6$, $R_7$ and $R_{15}$ have meanings as defined herein above, or a pharmaceutically acceptable salt thereof, by first coupling a compound of formula (X) with a boronic acid of the formula

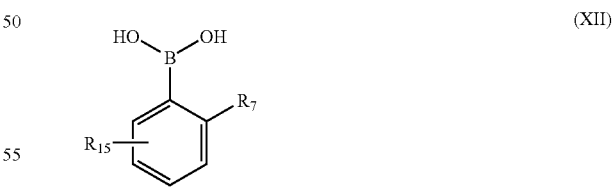

wherein $R_7$ and $R_{15}$ have meanings as defined herein above, followed by removal of the protecting group under appropriate reaction conditions, e.g., as illustrated herein above.

In addition, compounds of formula (IC') wherein $R_5$, $R_6$, $R_7$ and $R_{15}$ have meanings as defined herein above, and $R_1$ is —S(O)$_{0-2}$—X, —NR$_8$C(O)—X or —NR$_8$S(O)$_2$—X in which $R_8$ and X have meanings as defined herein above, may be prepared from compounds of formula (IV) using methods well known in the art.

Scheme 3:

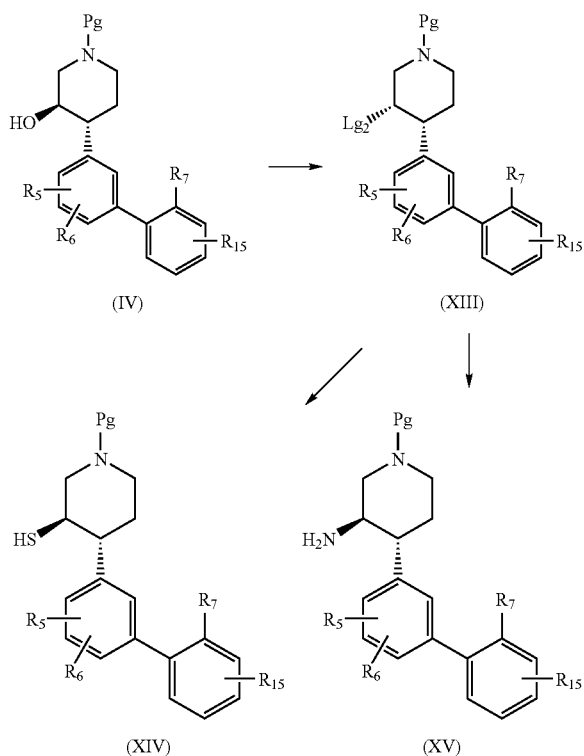

For example, as illustrated in Scheme 3, a compound of formula (IV) wherein Pg, $R_5$, $R_6$, $R_7$ and $R_{15}$ have meanings as defined herein above, may be converted to a compound of formula (XIV) or (XV), e.g., by first converting the hydroxyl group to a leaving group ($Lg_2$) such as bromide or iodide to afford a compound of formula (XIII) wherein Pg, $R_5$, $R_6$, $R_7$ and $R_{15}$ have meanings as defined above and $Lg_2$ represents a leaving group as described herein above. Subsequent reaction with a nucleophile, such as thioacetic acid or sodium azide, followed by hydrolysis or reduction, respectively, then affords a compound of formula (XIV) or a compound of formula (XV) wherein Pg, $R_5$, $R_6$, $R_7$ and $R_{15}$ have meanings as defined herein above. Compounds of formulae (XIV) or (XV) may the be converted to compounds of formula (IC') wherein $R_5$, $R_6$, $R_7$ and $R_{15}$ have meanings as defined herein above, and $R_1$ is —$S(O)_{0-2}$—X, —$NR_8$—X, —$NR_8C(O)$—X or —$NR_8S(O)_2$—X in which $R_8$ and X have meanings as defined herein above, using methods described herein or using methods well known in the art.

The processes described herein above may be conducted under inert atmosphere, preferably under nitrogen atmosphere.

As exemplified herein above, in starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, room temperature (RT) or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, diastereomers, optical isomers (antipodes), racemates or mixtures thereof. The aforesaid possible isomers or mixtures thereof are within the purview of this invention.

Any resulting mixtures of isomers can be separated on the basis of the physicochemical differences of the constituents, into the pure geometric or optical isomers, diastereomers, racemates, for example, by chromatography and/or fractional crystallization. Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the piperidinyl moiety may be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds, e.g., those of formula (IV), (IX), (XIV), (XV) and (IC'), may also be resolved by forming covalent diasteromeric derivatives, e.g. esters or amides, by condensing an alcohol or a thiol, e.g., those of formula (IV), (IX) or (XIV), or an amine, e.g., those of formula (XV) and (IC'), with a chiral, enantiomerically pure carboxylic acid. The resulting diastereomeric esters or amides can then be separated by crystallization or by chromatography and subsequently hydrolyzed to yield enantiomerically pure compounds of formula (IV), (IX), (XIV), (XV) and (IC'), respectively. Racemic products can also be resolved by chiral chromatography, e.g., high pressure liquid chromatography (HPLC) using a chiral adsorbent.

Finally, compounds of the invention are either obtained in the free form, as a salt thereof, or as prodrug derivatives thereof.

Compounds of the invention having basic groups, in particular, the piperidinyl moiety, can be converted into acid addition salts, especially pharmaceutically acceptable salts. These are formed, for example, with inorganic acids, such as mineral acids, for example, sulfuric acid, a phosphoric or hydrohalic acid, or with organic carboxylic acids, such as ($C_1$-$C_4$)-alkanecarboxylic acids which, for example, are unsubstituted or substituted by halogen, for example, acetic acid, such as saturated or unsaturated dicarboxylic acids, for example, oxalic, succinic, maleic or fumaric acid, such as hydroxycarboxylic acids, for example glycolic, lactic, malic, tartaric or citric acid, such as amino acids, for example, aspartic or glutamic acid, or with organic sulfonic acids, such as ($C_1$-$C_4$)-alkylsulfonic acids, for example, methanesulfonic acid; or arylsulfonic acids which are unsubstituted or substituted (for example by halogen). Preferred are salts formed with hydrochloric acid, methanesulfonic acid and maleic acid.

Compounds of the instant invention which contain acidic groups may be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

In view of the close relationship between the free compounds, the prodrug derivatives and the compounds in the form of their salts, whenever a compound is referred to in this context, a prodrug derivative and a corresponding salt is also intended, provided such is possible or appropriate under the circumstances.

The compounds, including their salts, can also be obtained in the form of their hydrates, or include other solvents used for their crystallization.

As described above, the compounds of the present invention are inhibitors of renin activity and, thus, may be employed for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the present invention are those suitable for enteral, such as oral or rectal, transdermal and parenteral administration to mammals, including man, to inhibit renin activity, and for the treatment of conditions associated with renin activity. Such conditions include hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and or polyvinylpyrrolidone; if desired
d) disintegrants, e.g., starches, agar, alginic acid or its sodium salt, or effervescent mixtures; and/or
e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and pre-determined rate over a prolonged period of time, and means to secure the device, to the skin.

Accordingly, the present invention provides pharmaceutical compositions as described above for the treatment of conditions mediated by renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:
a) antidiabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; peroxisome proliferator-activated receptor (PPAR) ligands; protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as LAF237;
b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;
c) anti-obesity agents such as orlistat; and
d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

Other specific anti-diabetic compounds are described by Patel Mona in *Expert Opin Investig Drugs,* 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents or anti-hypertensive agents, most preferably from antidiabetics, anti-hypertensive agents or hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

Thus, the present invention also relates to a compound of formula (I) for use as a medicament, to the use of a compound of formula (I) for the preparation of a pharmaceutical composition for the prevention and/or treatment of conditions mediated by renin activity, and to a pharmaceutical composition for use in conditions mediated by renin activity comprising a compound of formula (I), or a pharmaceutically acceptable salt thereof, in association with a pharmaceutically acceptable diluent or carrier therefor.

The present invention further provides a method for the prevention and/or treatment of conditions mediated by renin activity, which comprises administering a therapeutically effective amount of a compound of the present invention.

A unit dosage for a mammal of about 50-70 kg may contain between about 1 mg and 1000 mg, advantageously between about 5-600 mg of the active ingredient. The therapeutically effective dosage of active compound is dependent on the species of warm-blooded animal (mammal), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound of formula (I), or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents or anti-hypertensive agents. The kit may comprise instructions for its administration.

Similarly, the present invention provides a kit of parts comprising: (i) a pharmaceutical composition of the invention; and (ii) a pharmaceutical composition comprising a compound selected from an anti-diabetic, a hypolipidemic agent, an anti-obesity agent, an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula (I), or a pharmaceutically acceptable salt thereof, and a second drug substance, said second drug substance being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to modulation of renin activity.

Preferably, the condition associated with renin activity is selected from hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

Finally, the present invention provides a method or use which comprises administering a compound of formula (I) in combination with a therapeutically effective amount of an anti-diabetic agent, a hypolipidemic agent, an anti-obesity agent or an anti-hypertensive agent.

Ultimately, the present invention provides a method or use which comprises administering a compound of formula (I) in the form of a pharmaceutical composition as described herein.

As used throughout the specification and in the claims, the term "treatment" embraces all the different forms or modes of treatment as known to those of the pertinent art and in particular includes preventive, curative, delay of onset and/or progression, and palliative treatment.

The above-cited properties are demonstrable in vitro and in vivo tests using advantageously mammals, e.g., mice, rats, rabbits, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-10}$ molar concentrations. A therapeutically effective amount in vivo may range depending on the route of administration, between about 0.001 and 500 mg/kg, preferably between about 0.1 and 100 mg/kg.

As described above, the compounds of the present invention have enzyme-inhibiting properties. In particular, they inhibit the action of the natural enzyme renin. Renin passes from the kidneys into the blood where it effects the cleavage of angiotensinogen, releasing the decapeptide angiotensin I which is then cleaved in the lungs, the kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume which increase can be attributed to the action of angiotensin II. Inhibitors of the enzymatic activity of renin lead to a reduction in the formation of angiotensin I, and consequently a smaller amount of angiotensin II is produced. The reduced concentration of that active peptide hormone is the direct cause of the hypotensive effect of renin inhibitors.

The action of renin inhibitors may be demonstrated inter alis experimentally by means of in vitro tests, the reduction in the formation of angiotensin I being measured in various systems (human plasma, purified human renin together with synthetic or natural renin substrate).

Inter Ails the Following In Vitro Tests May be Used:

An extract of human renin from the kidney (0.5 mGU [milli-Goldblatt units]/mL) is incubated for one h at 37° C. and pH 7.2 in 1M aqueous 2-N-(tris-hydroxymethylmethyl) amino-ethanesulfonic acid buffer solution with 23 μg/mL of synthetic renin substrate, the tetradecapeptide H-Asp-Arg-Val-Tyr-Ile-His-ProPhe-His-Leu-Leu-Val-Tyr-Ser-OH. The amount of angiotensin I formed is determined by radioimmunoassay. Each of the inhibitors according to the invention is added to the incubation mixture at different concentrations. The $IC_{50}$ is defined as the concentration of a particular inhibitor that reduces the formation of angiotensin I by 50%.

Recombinant human renin (expressed in Chinese Hamster Ovary cells and purified using standard methods) at 4 nM concentration is incubated with test compound at various concentrations for 1 h at RT in 0.1M Tris-HCl buffer, pH 7.4, containing 0.05 M NaCl, 0.5 mM EDTA and 0.05% CHAPS. Synthetic peptide substrate Arg-Glu(EDANS)-Ile-His-Pro-Phe-His-Leu-Val-Ile_His_Thr-Lys(DABCYL)-Arg9 is added to a final concentration of 2 μM and increase in fluorescence is recorded at an excitation wave-length of 340 nm and at an emission wave-length of 485 nm in a microplate spectro-fluorimeter. $IC_{50}$ values are calculated from percentage of inhibition of renin activity as a function of test compound concentration (Fluorescence Resonance Energy Transfer, FRET, assay).

Recombinant human renin (expressed in Chinese Hamster Ovary cells and purified using standard methods) at 1 nM concentration is incubated with test compound at various concentrations for 1.5 h at 37° C. in 0.1M Tris/HCl pH 7.4 containing 0.05 M NaCl, 0.5 mM EDTA and 0.025% (w/v) CHAPS. Synthetic peptide substrate Ac-Ile-His-Pro-Phe-His-Leu-Val-Ile-His-Asn-Lys-[DY-505-X5] is added to a final concentration of 5 μM. The enzyme reaction is stopped by adding 6 μL of 1.0% TFA. The product of the reaction is separated by HPLC and quantified by spectrophotometric measurement at 505 nM wave-length. $IC_{50}$ values are calculated from percentage of inhibition of renin activity as a function of test compound concentration.

Recombinant human renin (expressed in Chinese Hamster Ovary cells and purified using standard methods) at 3.3 nM concentration, 125I-NVP-AJI891-NX-1 (0.27 μCi/mL) and streptavidin-SPA (0.67 mg/mL) beads are incubated with test compound at various concentrations for 2.0 h at RT in 0.1M Tris/HCl pH 7.4 containing 0.5M NaCl and 0.5% (w/v) Brij35. At the end of the incubation time, the plates are centrifuged (55 g, 60 seconds) and counted in a Wallac Micro-Beta reader. $IC_{50}$ values are calculated from percentage of displacement of radioligand binding to renin as a function of test compound concentration.

In animals deficient in salt, renin inhibitors bring about a reduction in blood pressure. Human renin may differ from the renin of other species. In order to test inhibitors of human renin, primates, e.g., marmosets (*Callithrix jacchus*) may be used, because human renin and primate renin are substantially homologous in the enzymatically active region. Inter alia the following in vivo tests may be used:

The test compounds are tested on normotensive marmosets of both sexes having a body weight of approximately 350 g that are conscious, allowed to move freely and in their normal cages. The blood pressure and heart rate are measured via a catheter in the descending aorta and recorded radiometrically. The endogenous release of renin is stimulated by the combination of a 1-week low-salt diet and a single intramuscular injection of furosemide (5-(aminosulfonyl)-4-chloro-2-[(2-furanylmethyl)amino]benzoic acid) (5 mg/kg). 16 h after the injection of furosemide the test compounds are administered either directly into the femoral artery using an injection cannula or, in the form of a suspension or solution, via an oesophageal tube into the stomach, and their action on the blood pressure and heart rate are evaluated. In the in vivo test described, the compounds of the present invention have hypotensive action at doses of from approximately 0.003 to approximately 1 mg/kg i.v. and at doses of from approximately 0.3 to approximately 100 mg/kg p.o.

Alternatively, renin inhibitors may be tested on male normotensive marmosets weighing 250 to 500 g that are conscious, allowed to move freely and in their normal cages. The blood pressure, and heart rate are measured via a catheter placed in the descending aorta and recorded radiometrically. Electrocardiogram are obtained by placing electrodes of transmitter in lead II. The endogenous release of renin is stimulated by two intramuscular injection of furosemide (5-(aminosulfonyl)-4-chloro-2-[(2-furanylmethyl)amino]benzoic acid) (10 mg/kg) 43 and 19 hours prior compound application. Test compounds are administered either directly into the femoral artery using an injection cannula or, in the form of a suspension or solution, via an oesophageal tube into the stomach, and their action on the blood pressure, heart rate and ECG are evaluated. In the in vivo test described, compounds of the present invention have hypotensive action at doses of from approximately 0.003 to approximately 0.3 mg/kg i.v. and at doses of from approximately 0.31 to approximately 30 mg/kg p.o.

The compounds of the present invention also have the property of regulating, especially reducing, intra-ocular pressure.

The extent of the reduction in intra-ocular pressure after administration of a pharmaceutical active ingredient of formula (I) according to the present invention can be determined, for example, in animals, for example rabbits or monkeys. Two typical experimental procedures that illustrate the present invention, but are not limited to in any way, are described hereinafter.

The in vivo test on a rabbit of the "Fauve de Bourgogne" type to determine the intra-ocular-pressure-reducing activity of topically applied compositions can be designed, for example, as follows: The intra-ocular pressure (IOP) is measured using an aplanation tonometer both before the experiment and at regular intervals of time. After a local anaesthetic has been administered, the suitably formulated test compound is applied topically in a precisely defined concentration (e.g. 0.000001-5% by weight) to one eye of the animal in question. The contralateral eye is treated, for example, with physiological saline. The measured values thus obtained are evaluated statistically.

The in vivo tests on monkeys of the species *Macaca Fascicularis* to determine the intra-ocular-pressure-reducing activity of topically applied compositions can be carried out, e.g., as follows: The suitably formulated test compound is applied in a precisely defined concentration (e.g. 0.000001-5% by weight) to one eye of each monkey. The other eye of the monkey is treated correspondingly, for example with physiological saline. Before the start of the test the animals are anaesthetised with intramuscular injections of, for example, ketamine. At regular intervals of time, the intra-ocular pressure (IOP) is measured. The test is carried out and evaluated in accordance with the rules of "good laboratory practice" (GLP).

Illustrative of the invention, the compound of Example 1 demonstrates inhibition of renin activity with an $IC_{50}$ value of about 70 nM in the FRET assay.

The following Examples are intended to illustrate the invention and are not to be construed as being limitations thereon. If not mentioned otherwise, all evaporations are performed under reduced pressure, preferably between about 10 and 100 mmHg (=20-133 mbar). The structure of final products, intermediates and starting materials is confirmed by standard analytical methods, e.g., microanalysis, melting point (m.p.) and spectroscopic characteristics, e.g., MS, LC/MS, IR, NMR. In general, abbreviations used are those conventional in the art.

EXAMPLE 1

(3R*,4R*)-4-Biphenyl-3-yl-3-(naphthalen-2-yl-methoxy)-piperidine hydrochloride

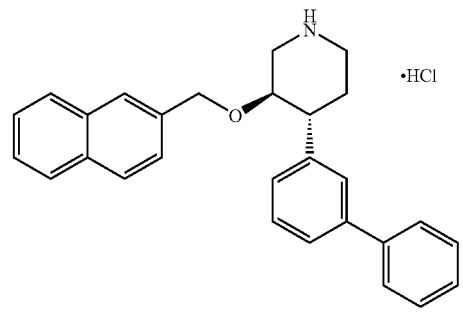 [SMILES: c1ccc(-c2cccc([C@H]3CCNC[C@@H]3OCc3ccc4ccccc4c3)c2)cc1 ; Cl]

A. 4-Biphenyl-3-yl-3,6,dihydro-2H-pyridine-1-carboxylic acid t-butyl ester

A stirred mixture of 4-trifluoromethanesulfonyloxy-3,6-dihydro-2H-pyridine-1-carboxylic acid tert-butyl ester (3.98 g, 12 mmol), 3-biphenylboronic acid (2.77 g, 14 mmol), LiCl (1.53 g, 36 mmol), dimethoxyethane (35 mL), tetrakis-(triphenylphosphin)-palladium (0.81 g, 0.7 mmol) and $Na_2CO_3$ (2M solution, 14 mL, 28 mmol) is heated at reflux under argon for 14 h. The mixture is cooled to RT, dimethoxyethane is removed in vacuo and the residue is diluted with aqueous 2N $Na_2CO_3$ solution containing a few mL of concentrated $NH_4OH$. The aqueous layer is extracted three times with $CH_2Cl_2$. The combined organic extracts are dried ($Na_2SO_4$) and evaporated in vacuo. Flash chromatography of the dark residue ($SiO_2$, hexane/ethyl acetate) affords 4-biphenyl-3-yl-3,6,dihydro-2H-pyridine-1-carboxylic acid t-butyl ester as a colourless oil: MS (after treatment with trifluoroacetic acid) 236.3 $[M+H—C_5H_8O_2]^+$; $R_f$ 0.40 (hexane/ethyl acetate 8:2).

B. (3R*,4R*)-4-Biphenyl-3-yl-3-hydroxy-piperidine-1-carboxylic acid t-butyl ester To a stirred mixture of the title A compound, 4-biphenyl-3-yl-3,6,dihydro-2H-pyridine-1-carboxylic acid t-butyl ester (2.57 g, 7.66 mmol) and 6 mL of dry THF is added dropwise under argon at 5° C. a 1M borane-tetrahydrofuran complex solution (11 mL, 11 mmol) within 15 min. The reaction mixture is stirred for 10 min. at 5° C. and for 1 h at RT. NaBO$_3$ (3.38 g, 22 mmol) is then added in several portions followed by H$_2$O (10 mL). After 2 h at RT, the reaction mixture is extracted twice with ethyl acetate. The combined organic extracts are dried (Na$_2$SO$_4$) and evaporated in vacuo. Flash chromatography of the residue (SiO$_2$, hexane/ethyl acetate) affords (3R*,4R*)-4-biphenyl-3-yl-3-hydroxy-piperidine-1-carboxylic acid t-butyl ester as a white amorphous solid: MS (after treatment with trifluoroacetic acid) 254.3 [M+H—C$_5$H$_8$O$_2$]$^+$; R$_f$ 0.10 (hexane/ethyl acetate 8:2).

C. (3R*,4R*)-4-Biphenyl-3-yl-3-(naphthalen-2-yl-methoxy)-piperidine-1-carboxylic acid t-butyl ester A suspension of the title B compound, (3R*,4R*)-4-biphenyl-3-yl-3-hydroxy-piperidine-1-carboxylic acid t-butyl ester (318 mg, 0.9 mmol) and sodium hydride (60% dispersion in mineral oil, 72 mg, 1.8 mmol) in 8 mL of dry DMA is shaken for 10 min. at 50° C. After cooling to RT, 2-(bromomethyl)naphthalene (298 mg, 1.35 mmol) is added and the mixture shaken for 16 h at 50° C. After addition of H$_2$O, the aqueous layer is extracted twice with ethyl acetate. The combined organic extracts are dried (Na$_2$SO$_4$) and evaporated in vacuo. Flash chromatography of the residue (SiO$_2$, hexane/ethyl acetate) affords (3R*,4R*)-4-biphenyl-3-yl-3-(naphthalen-2-ylmethoxy)-piperidine-1-carboxylic acid tert-butyl ester as a yellowish viscous oil: MS (LC/MS) 494.2 [M+H]$^+$; R$_f$ 0.30 (hexane/ethyl acetate 8:2).

D. (3R*,4R*)-4-Biphenyl-3-yl-3-(naphthalen-2-yl-methoxy)-piperidine hydrochloride A mixture of the title C compound, (3R*,4R*)-4-biphenyl-3-yl-3-(naphthalen-2-ylmethoxy)-piperidine-1-carboxylic acid t-butyl ester (54 mg, 0.11 mmol) and HCl (5M in 2-propanol, 1 mL, 5 mmol) is stirred for several h at RT (until complete consumption of the starting material). The reaction mixture is evaporated in vacuo to afford (3R*,4R*)-4-biphenyl-3-yl-3-(naphthalen-2-ylmethoxy)-piperidine hydrochloride as a slightly beige foam: MS (LC/MS) 394.1 [M+H]$^+$; R$_f$ 0.23 (DCM/MeOH 9:1).

EXAMPLE 2

(3R*,4R*)-4-Biphenyl-3-yl-3-(biphenyl-4-yl-methoxy)-piperidine hydrochloride

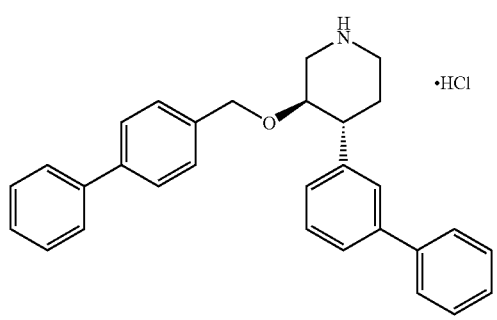 [SMILES: c1ccc(-c2ccc(CO[C@H]3CNCC[C@@H]3c3cccc(-c4ccccc4)c3)cc2)cc1 ; Cl]

The title compound is prepared analogously as described in Example 1: MS 420.6 [M+H]$^+$; retention time 2.77 min (HPLC, Nucleosil C18; 30→100% CH$_3$CN in H$_2$O within 3 min).

EXAMPLE 3

(3R*,4R*)-3-Benzyloxy-4-biphenyl-3-yl-piperidine hydrochloride

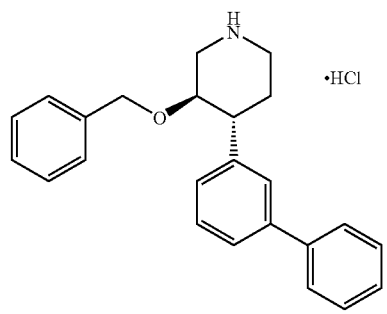 [SMILES: c1ccc(CO[C@H]2CNCC[C@@H]2c2cccc(-c3ccccc3)c2)cc1 ; Cl]

The title compound is prepared analogously as described in Example 1: MS (LC/MS) 344.2 [M+H]$^+$; R$_f$ 0.20 (DCM/MeOH 9:1).

EXAMPLE 4

(3R*,4R*)-4-Biphenyl-3-yl-3-(4-bromo-benzyloxy)-piperidine hydrochloride

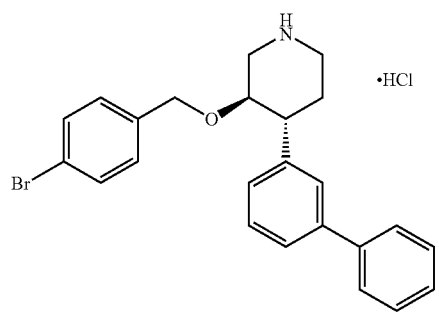 [SMILES: Brc1ccc(CO[C@H]2CNCC[C@@H]2c2cccc(-c3ccccc3)c2)cc1 ; Cl]

The title compound is prepared analogously as described in Example 1: MS (LC/MS) 422.1/424.1 [M+H]$^+$; R$_f$ 0.22 (DCM/MeOH 9:1).

EXAMPLE 5

(3R*,4R*)-4-Biphenyl-3-yl-3-(4-trifluoromethoxy-benzyloxy)-piperidine hydrochloride

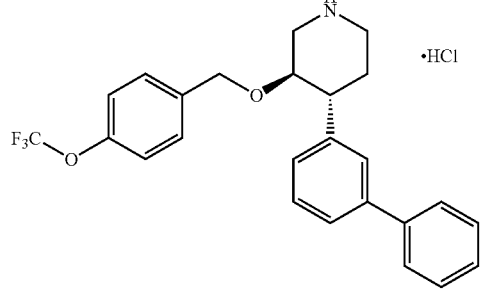

The title compound is prepared analogously as described in Example 1: MS (LC/MS) 428.2 [M+H]⁺; R$_f$ 0.19 (DCM/MeOH 9:1).

EXAMPLE 6

(3R*,4R*)-4-Biphenyl-3-yl-3-(3-phenoxy-benzyloxy)-piperidine hydrochloride

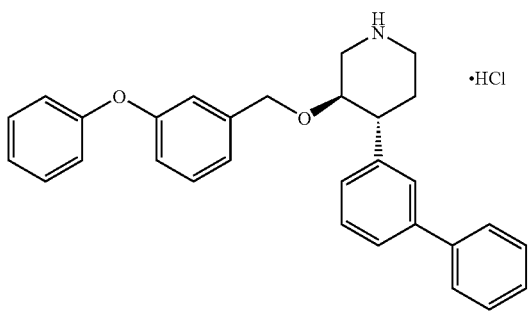 [SMILES: c1ccc(Oc2cccc(CO[C@H]3CNCC[C@@H]3c3cccc(-c4ccccc4)c3)c2)cc1 ; Cl]

The title compound is prepared analogously as described in Example 1: MS (LC/MS) 436.2 [M+H]⁺; R$_f$ 0.26 (DCM/MeOH 9:1).

EXAMPLE 7

(3R*,4R*)-4-Dibenzofuran-4-yl-3-(naphthalen-2-ylmethoxy)-piperidine hydrochloride

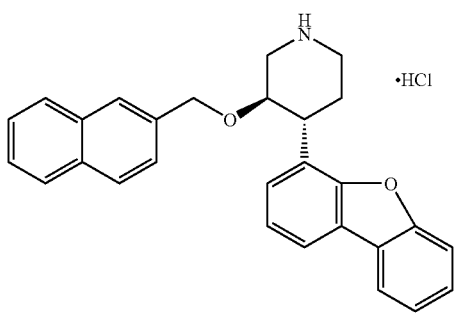 [SMILES: c1ccc2cc(CO[C@H]3CNCC[C@@H]3c3cccc4c3oc3ccccc34)ccc2c1 ; Cl]

A mixture of (3R*,4R*)-4-dibenzofuran-4-yl-3-(naphthalen-2-ylmethoxy)-piperidine-1-carboxylic acid t-butyl ester (prepared analogously as described in Example 1; 191 mg, 0.38 mmol) and HCl (5 M in 2-propanol, 2 mL, 10 mmol) is stirred for 1 h at RT. The solvent is removed in vacuo and the residue purified by preparative HPLC (CH$_3$CN/H$_2$O). A saturated aqueous NaHCO$_3$ solution is added to the combined pure fractions, CH$_3$CN is evaporated in vacuo, and the remaining aqueous layer extracted twice with DCM. The combined organic phases are dried (Na$_2$SO$_4$) and evaporated. The resulting gum is treated with HCl (4M in 1,4-dioxane, 1 mL) and stirred for 30 min at RT. Evaporation of the solvent in vacuo yields (3R*,4R*)-4-dibenzofuran-4-yl-3-(naphthalen-2-ylmethoxy)-piperidine hydrochloride as a white solid: MS 408.6 [M+H]⁺; R$_f$ 0.20 (DCM/MeOH 9:1).

EXAMPLE 8

(3R*,4R*)-3-(Biphenyl-4-ylmethoxy)-4-dibenzofuran-4-yl-piperidine hydrochloride

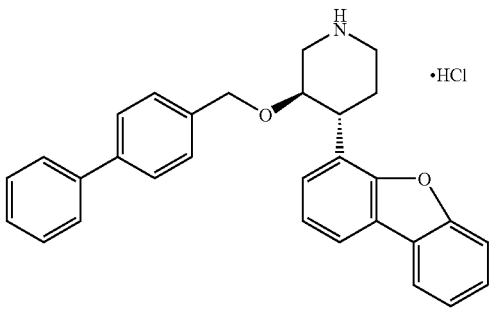 [SMILES: c1ccc(-c2ccc(CO[C@H]3CNCC[C@@H]3c3cccc4c3oc3ccccc34)cc2)cc1 ; Cl]

A mixture of (3R*,4R*)-3-(biphenyl-4-ylmethoxy)-4-dibenzofuran-4-yl-piperidine-1-carboxylic acid t-butyl ester (prepared analogously as described in Example 1; 218 mg, 0.41 mmol) and HCl (5M in 2-propanol, 2 mL, 10 mmol) is stirred for 1 h at RT. The solvent is removed in vacuo, the residue triturated with hot MeOH and the suspension filtered. The filter cake is washed with MeOH and ether and dried at 60° C. in vacuo to afford (3R*,4R*)-3-(biphenyl-4-ylmethoxy)-4-dibenzofuran-4-yl-piperidine hydrochloride: MS 434.6 [M+H]⁺; R$_f$ 0.23 (DCM/MeOH 9:1).

EXAMPLE 9

(3R*,4R*)-3-Benzyloxy-4-dibenzofuran-4-yl-piperidine hydrochloride

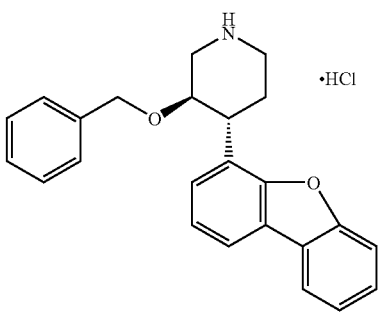 [SMILES: c1ccc(CO[C@H]2CNCC[C@@H]2c2cccc3c2oc2ccccc23)cc1 ; Cl]

The title compound is prepared analogously as described in Example 8: MS 358.4 [M+H]⁺; R$_f$ 0.19 (DCM/MeOH 9:1).

EXAMPLE 10

(3R*,4R*)-4-Dibenzofuran-4-yl-3-(3-phenoxy-benzyloxy)-piperidine hydrochloride

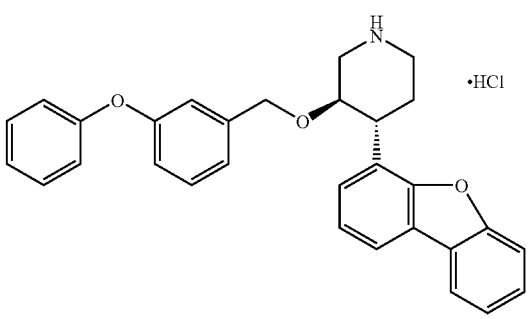 [SMILES: c1ccc(Oc2cccc(CO[C@H]3CNCC[C@@H]3c3cccc4c3oc3ccccc34)c2)cc1 ; Cl]

The title compound is prepared analogously as described in Example 8: MS 450.7 [M+H]⁺; R$_f$ 0.23 (DCM/MeOH 9:1).

EXAMPLE 11

[3-((3R*,4R*)-4-Dibenzofuran-4-yl-piperidin-3-yloxymethyl)-phenyl]-phenyl-methanone hydrochloride

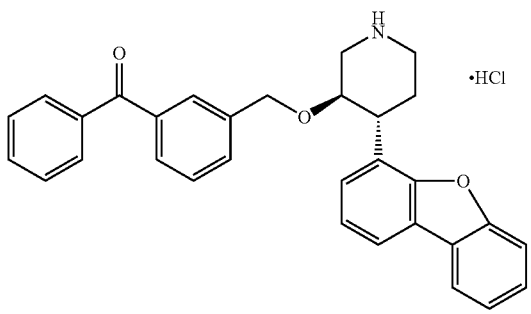 [SMILES: O=C(c1ccccc1)c1cccc(CO[C@H]2CNCC[C@@H]2c2cccc3c2oc2ccccc23)c1 ; Cl]

The title compound is prepared analogously as described in Example 8: MS 462.6 [M+H]$^+$; R$_f$ 0.21 (DCM/MeOH 9:1).

EXAMPLE 12

(3R*,4R*)-4-(4'-Methoxy-biphenyl-3-yl)-3-(naphthalen-2-ylmethoxy)-piperidine hydrochloride

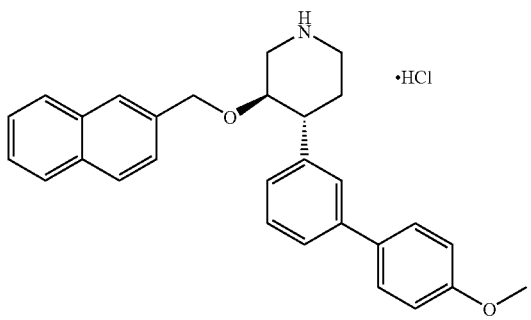 [SMILES: COc1ccc(-c2cccc([C@H]3CCNC[C@@H]3OCc3ccc4ccccc4c3)c2)cc1 ; Cl]

A. (3-Hydroxy-phenyl)-3,6,dihydro-2H-pyridine-1-carboxylic acid t-butyl ester The title compound is prepared analogously as described for the title A compound in Example 1 using 3-hydroxyphenylboronic acid: MS 274.3 [M−H]$^-$; retention time 6.23 min (HPLC, Nucleosil C18; 5→100% CH$_3$CN in H$_2$O within 8 min).

B. (3R*,4R*)-3-Hydroxy-4-(4'-methoxy-biphenyl-3-yl)-piperidine-1-carboxylic acid t-butyl ester A mixture of (3-hydroxy-phenyl)-3,6-dihydro-2H-pyridine-1-carboxylic acid t-butyl ester (1.0 g, 3.63 mmol) and triethylamine (1.02 mL, 7.26 mmol) in 100 mL CH$_2$Cl$_2$ is stirred for 10 min. at RT. After the addition of N-phenyltrifluoromethanesulfonimide (1.56 g, 4.36 mmol) and K$_2$CO$_3$, the reaction mixture is heated at reflux for 5 h. The mixture is cooled to RT, filtered and the solvent removed in vacuo. Filtration of the residue (SiO$_2$, hexane/ethyl acetate) affords crude 4-(3-trifluoromethanesulfonyloxy-phenyl)-3,6-dihydro-2H-pyridine-1-carboxylic acid t-butyl ester as a colourless oil. The crude product is dissolved in 12 mL dimethoxyethane. After the addition of 4-methoxyphenylboronic acid (669 mg, 4.4 mmol), LiCl (466 mg, 11 mmol), tetrakis-(triphenylphosphin)-palladium (0.25 g, 0.22 mmol) and Na$_2$CO$_3$ (2M solution, 4.4 mL, 8.8 mmol) the mixture is heated at reflux under argon for 12 h. The mixture is cooled to RT, dimethoxyethane is removed in vacuo and the residue is diluted with ethyl acetate. The organic layer is washed with aqueous 2M Na$_2$CO$_3$ sol., dried (Na$_2$SO$_4$) and evaporated in vacuo. Flash chromatography of the brown residue (SiO$_2$, hexane/ethyl acetate) affords 4-(4'-methoxy-biphenyl-3-yl-3,6,dihydro-2H-pyridine-1-carboxylic acid t-butyl ester as a yellow oil.

To a stirred mixture of this compound (858 mg, 2.35 mmol) in 6 mL of dry THF is added dropwise under argon at 5° C. a 1M borane-tetrahydrofuran complex solution (3.84 mL, 3.84 mmol) within 10 min. The reaction mixture is stirred for 10 min. at 5° C. and for 1 h at RT. NaBO$_3$ (1.18 g, 7.68 mmol) is then added in several portions followed by H$_2$O (2.25 mL). After 4 h at RT, the reaction mixture is diluted with brine and extracted twice with ethyl acetate. The combined organic extracts are dried (Na$_2$SO$_4$) and evaporated in vacuo. Flash chromatography of the residue (SiO$_2$, hexane/ethyl acetate) affords (3R*,4R*)-3-hydroxy-4-(4'-methoxy-biphenyl-3-yl)-piperidine-1-carboxylic acid t-butyl ester as a white amorphous solid: MS 384.4 [M+H]$^+$; retention time 7.01 min (HPLC, Nucleosil C18; 5→100% CH$_3$CN in H$_2$O within 8 min).

C. (3R*,4R*)-4-(4'-Methoxy-biphenyl-3-yl)-3-(naphthalen-2-ylmethoxy)-piperidine-1-carboxylic acid t-butyl ester The title compound is prepared analogously as described for the title C compound in Example 1 from the title B compound, (3R*,4R*)-3-hydroxy-4-(4'-methoxy-biphenyl-3-yl)-piperidine-1-carboxylic acid t-butyl ester: MS 524.5 [M+H]$^+$; retention time 8.83 min (HPLC, Nucleosil C18; 5→100% CH$_3$CN in H$_2$O within 8 min, then 100% CH$_3$CN for 2 min).

D. (3R*,4R*)-4-(4'-Methoxy-biphenyl-3-yl)-3-(naphthalen-2-ylmethoxy)-piperidine hydrochloride The title compound is prepared analogously as described for the title D compound in Example 1 from (3R*,4R*)-4-(4'-methoxy-biphenyl-3-yl)-3-(naphthalen-2-ylmethoxy)-piperidine-1-carboxylic acid t-butyl ester: MS 424.5 [M+H]$^+$; R$_f$ 0.24 (DCM/MeOH 9:1).

EXAMPLE 13

3'-[(3R*,4R*)-3-(Naphthalen-2-ylmethoxy)-piperidin-4-yl]-biphenyl-3-ol hydrochloride

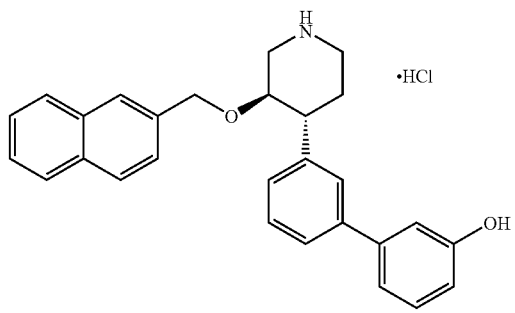 [SMILES: Oc1cccc(-c2cccc([C@H]3CCNC[C@@H]3OCc3ccc4ccccc4c3)c2)c1 ; Cl]

A. 4-(3-Bromo-phenyl)-3,6-dihydro-2H-pyridine-1-carboxylic acid t-butyl ester A stirred mixture of 4-(4,4,5,5-tetramethyl-[1,3,2]dioxaborolan-2-yl)-3,6-dihydro-2H-pyridine-1-carboxylic acid tert-butyl ester (prepared as described in Tetrahedron Letters 2000, 3705-3708; 6.52 g, 21.1 mmol), 1-bromo-3-iodobenzene (4.05 mL, 31.8 mmol), bis-(triphenyl-phosphine)-palladium(II) chloride (892 mg, 1.27 mmol), $K_2CO_3$ (8.7 g, 63 mmol) and 1,1'-bis(diphenylphosphino)ferrocene (704 mg, 1.27 mmol) in 120 mL dimethylformamide is heated at 80° C. under argon for 14 h. The mixture is cooled to RT, dimethylformamide is removed in vacuo. After addition of brine, the aqueous layer is extracted three times with $CH_2Cl_2$. The combined organic extracts are dried ($Na_2SO_4$) and evaporated in vacuo. Flash chromatography of the residue ($SiO_2$, hexane/ethyl acetate) affords 4-(3-bromo-phenyl)-3,6-dihydro-2H-pyridine-1-carboxylic acid t-butyl ester as a colourless viscous resin: MS 338.2/340.2 [M+H]$^+$; retention time 8.01 min (HPLC, Nucleosil C18; 5→100% $CH_3CN$ in $H_2O$ within 8 min, then 100% $CH_3CN$ for 2 min).

B. (3R*,4R*)-4-(3-Bromo-phenyl)-3-hydroxy-piperidine-1-carboxylic acid t-butyl ester The title compound is prepared analogously as described for the title B compound in Example 1 from the title A compound, 4-(3-bromo-phenyl)-3,6-dihydro-2H-pyridine-1-carboxylic acid t-butyl ester: MS 356.2/358.1 [M+H]$^+$; retention time 6.59 min (HPLC, Nucleosil C18; 5→100% $CH_3CN$ in $H_2O$ within 8 min).

C. (3R*,4R*)-4-(3-Bromo-phenyl)-3-(naphthalen-2-ylmethoxy)-piperidine-1-carboxylic acid t-butyl ester The title compound is prepared analogously as described for the title C compound in Example 1 from the title B compound, (3R*,4R*)-4-(3-bromo-phenyl)-3-hydroxy-piperidine-1-carboxylic acid t-butyl ester: MS 496.3/498.2 [M+H]$^+$; retention time 8.87 min (HPLC, Nucleosil C18; 5-100% $CH_3CN$ in $H_2O$ within 8 min, then 100% $CH_3CN$ for 2 min).

D. (3R*,4R*)-4-(3'-Hydroxy-biphenyl-3-yl)-3-(naphthalen-2-ylmethoxy)-piperidine-1-carboxylic acid t-butyl ester A stirred mixture of (3R*,4R*)-4-(3-bromo-phenyl)-3-(naphthalen-2-ylmethoxy)-piperidine-1-carboxylic acid t-butyl ester (150 mg, 0.3 mmol), 3-hydroxyphenylboronic acid (48 mg, 0.35 mmol), dimethoxyethane (3 mL), $H_2O$ (1 mL), tetrakis-(triphenylphosphin)-palladium (21 mg, 0.02 mmol) and $Na_2CO_3$ (47 mg, 0.45 mmol) is heated at reflux under argon for 16 h. The mixture is cooled to RT, dimethoxyethane is removed in vacuo and the residue is diluted with aqueous 2N $Na_2CO_3$ solution containing a few mL of concentrated $NH_4OH$. The aqueous layer is extracted three times with $CH_2Cl_2$. The combined organic extracts are dried ($Na_2SO_4$) and evaporated in vacuo. Flash chromatography of the dark residue ($SiO_2$, hexane/ethyl acetate) affords (3R*,4R*)-4-(3'-hydroxy-biphenyl-3-yl)-3-(naphthalen-2-ylmethoxy)-piperidine-1-carboxylic acid t-butyl ester as a yellowish resin: MS 508.4 [M–H]$^-$; retention time 8.01 min (HPLC, Nucleosil C18; 5-100% $CH_3CN$ in $H_2O$ within 8 min, then 100% $CH_3CN$ for 2 min).

E. 3'-[(3R*,4R*)-3-(Naphthalen-2-ylmethoxy)-piperidin-4-yl]-biphenyl-3-ol hydrochloride A mixture of (3R*,4R*)-4-(3'-hydroxy-biphenyl-3-yl)-3-(naphthalen-2-ylmethoxy)-piperidine-1-carboxylic acid t-butyl ester (96.5 mg, 0.19 mmol) and HCl (5M in 2-propanol, 2 mL, 10 mmol) is stirred for 1 h at RT. The reaction mixture is evaporated in vacuo and the residue purified using preparative HPLC ($H_2O/CH_3CN$). The combined pure fractions are treated with solid $K_2CO_3$ and $CH_3CN$ is removed in vacuo. The aqueous layer is extracted twice with $CH_2Cl_2$. The combined organic extracts are dried ($Na_2SO_4$) and evaporated in vacuo. The residue is stirred with HCl (4M in dioxane, 1 mL, 8 mmol) for 30 min. at RT. Evaporation of the solvent affords 3'-[(3R*,4R*)-3-(naphthalen-2-ylmethoxy)-piperidin-4-yl]-biphenyl-3-ol hydrochloride as a colourless white solid: MS 410.5 [M+H]$^+$; $R_f$ 0.11 (DCM/MeOH 9:1).

EXAMPLE 14

(3R*,4R*)-4-[3'-(2-Methoxy-ethoxy)-biphenyl-3-yl]-3-(naphthalen-2-ylmethoxy)-piperidine hydrochloride

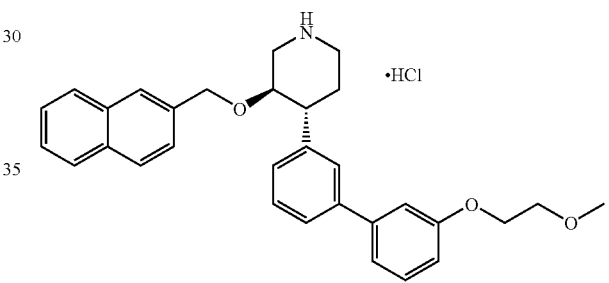

A mixture of the title D compound in Example 13, (3R*,4R*)-4-(3'-hydroxy-biphenyl-3-yl)-3-(naphthalen-2-ylmethoxy)-piperidine-1-carboxylic acid t-butyl ester (80 mg, 0.16 mmol), 2-chloroethyl methyl ether (57 µL, 0.62 mmol), $K_2CO_3$ (29 mg, 0.21 mmol), KI (16.6 mg, 0.1 mmol) and dimethylacetamide (1.5 mL) is stirred under argon for 16 h at 75° C. After the addition of a second portion of 2-chloroethyl methyl ether (35 µL, 0.38 mmol) and $K_2CO_3$ (44 mg, 0.32 mmol) stirring is continued for 18 h at 75° C. The mixture is filtered and the filtrate evaporated in vacuo. HCl (5M in 2-propanol, 1 mL, 5 mmol) is added to the crude residue and the mixture is stirred for 45 min. at RT. The reaction mixture is evaporated in vacuo and the residue purified using preparative HPLC ($H_2O/CH_3CN$). The combined pure fractions are treated with solid $K_2CO_3$ and $CH_3CN$ is removed in vacuo. The aqueous layer is extracted twice with $CH_2Cl_2$. The combined organic extracts are dried ($Na_2SO_4$) and evaporated in vacuo. The residue is stirred with HCl (5M in 2-propanol, 1 mL, 5 mmol) for 30 min. at RT. Evaporation of the solvent affords (3R*,4R*)-4-[3'-(2-methoxy-ethoxy)-biphenyl-3-yl]-3-(naphthalen-2-ylmethoxy)-piperidine hydrochloride as a brownish amorphous solid: MS (LC/MS) 468.4 [M+H]$^+$; retention time 5.85 min (HPLC, Nucleosil C18; 5→100% $CH_3CN$ in $H_2O$ within 8 min).

EXAMPLE 15

N-{3'-[(3R*,4R*)-3-(Naphthalen-2-ylmethoxy)-piperidin-4-yl]-biphenyl-3-yl}-acetamide hydrochloride

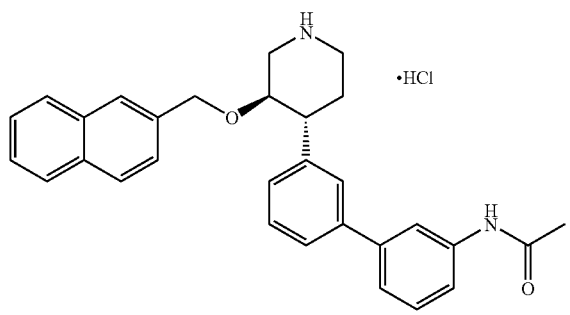 [SMILES: CC(=O)Nc1cccc(-c2cccc([C@H]3CCNC[C@@H]3OCc3ccc4ccccc4c3)c2)c1 ; Cl]

The title compound is prepared analogously as described in Example 13 using 3-acetamidobenzeneboronic acid: MS 451.5 [M+H]$^+$; R$_f$ 0.11 (DCM/MeOH 9:1).

EXAMPLE 16

1-{3'-[(3R*,4R*)-3-(Naphthalen-2-ylmethoxy)-piperidin-4-yl]-biphenyl-4-yl}-ethanone hydrochloride

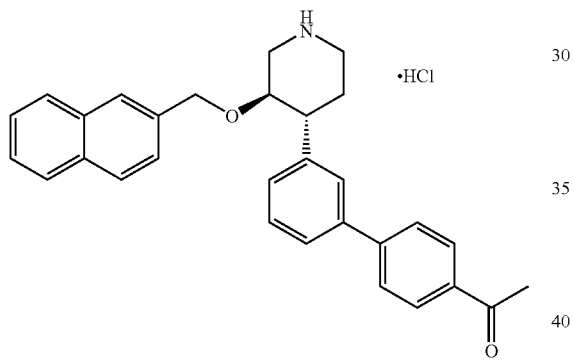

The title compound is prepared analogously as described in Example 13 using 4-acetylphenylboronic acid: MS 436.6 [M+H]$^+$; R$_f$ 0.24 (DCM/MeOH 9:1).

EXAMPLE 17

1-{3'-[(3R*,4R*)-3-(Naphthalen-2-ylmethoxy)-piperidin-4-yl]-biphenyl-3-yl}-ethanone hydrochloride

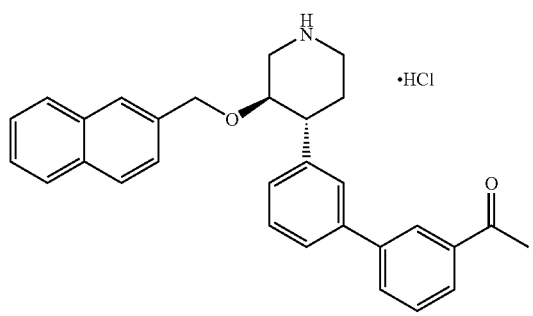 [SMILES: CC(=O)c1cccc(-c2cccc([C@H]3CCNC[C@@H]3OCc3ccc4ccccc4c3)c2)c1 ; Cl]

The title compound is prepared analogously as described in Example 13 using 3-acetylphenylboronic acid: MS 436.6 [M+H]$^+$; R$_f$ 0.24 (DCM/MeOH 9:1).

EXAMPLE 18

3'-[(3R*,4R*)-3-(Naphthalen-2-ylmethoxy)-piperidin-4-yl]-biphenyl-3-carboxylic acid ethyl ester hydrochloride

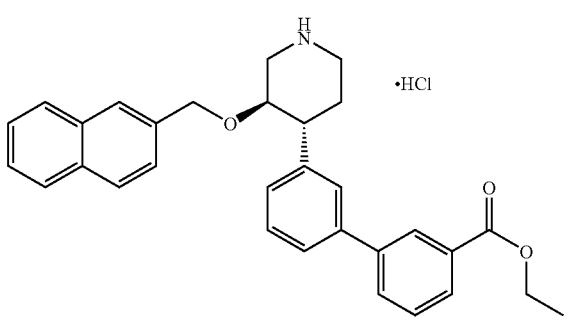 [SMILES: CCOC(=O)c1cccc(-c2cccc([C@H]3CCNC[C@@H]3OCc3ccc4ccccc4c3)c2)c1 ; Cl]

The title compound is prepared analogously as described in Example 13 using 3-ethoxycarbonylphenylboronic acid: MS 466.5 [M+H]$^+$; R$_f$ 0.28 (DCM/MeOH 9:1).

EXAMPLE 19

(3R*,4R*)-4-(3'-Chloro-biphenyl-3-yl)-3-(naphthalen-2-ylmethoxy)-piperidine hydrochloride

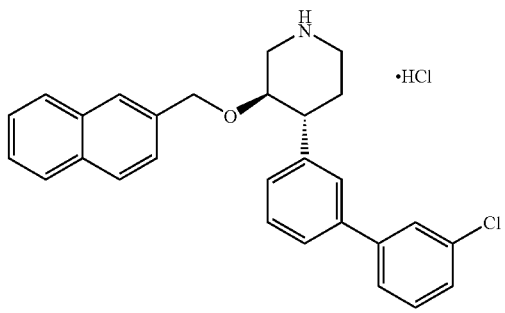 [SMILES: Clc1cccc(-c2cccc([C@H]3CCNC[C@@H]3OCc3ccc4ccccc4c3)c2)c1 ; Cl]

The title compound is prepared analogously as described in Example 13 using 3-chlorophenylboronic acid: MS 428.4 [M+H]$^+$; R$_f$ 0.27 (DCM/MeOH 9:1).

EXAMPLE 20

(3R*,4R*)-3-(Naphthalen-2-ylmethoxy)-4-(3'-trifluoromethyl-biphenyl-3-yl)-piperidine hydrochloride

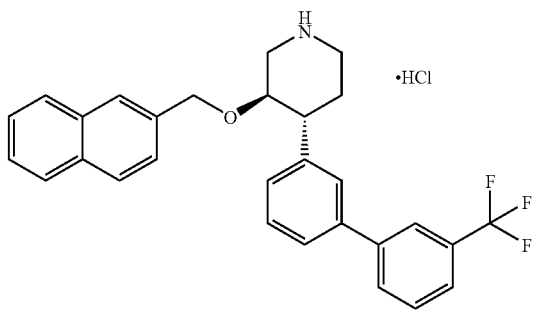 [SMILES: FC(F)(F)c1cccc(-c2cccc([C@H]3CCNC[C@@H]3OCc3ccc4ccccc4c3)c2)c1 ; Cl]

The title compound is prepared analogously as described in Example 13 using 3-(trifluoromethyl)phenylboronic acid: MS 462.5 [M+H]⁺; $R_f$ 0.25 (DCM/MeOH 9:1).

EXAMPLE 21

(3R*,4R*)-4-(4'-Chloro-biphenyl-3-yl)-3-(naphthalen-2-ylmethoxy)-piperidine hydrochloride

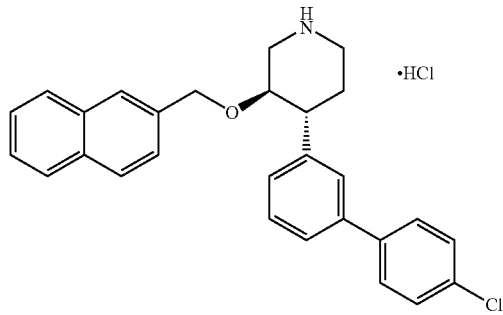 [SMILES: Clc1ccc(-c2cccc([C@H]3CCNC[C@@H]3OCc3ccc4ccccc4c3)c2)cc1 ; Cl]

The title compound is prepared analogously as described in Example 13 using 4-chlorophenylboronic acid: MS 428.4 [M+H]⁺; $R_f$ 0.25 (DCM/MeOH 9:1).

EXAMPLE 22

3'-[(3R*,4R*)-3-(Naphthalen-2-ylmethoxy)-piperidin-4-yl]-biphenyl-4-ol hydrochloride

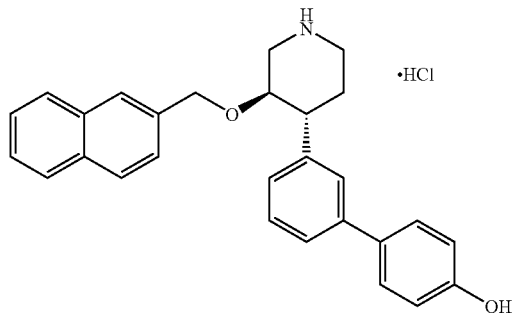 [SMILES: Oc1ccc(-c2cccc([C@H]3CCNC[C@@H]3OCc3ccc4ccccc4c3)c2)cc1 ; Cl]

The title compound is prepared analogously as described in Example 13 using 4-(t-butyldimethylsilyloxy)phenylboronic acid: MS 410.6 [M+H]⁺; $R_f$ 0.12 (DCM/MeOH 9:1).

EXAMPLE 23

Dimethyl-{3'-[(3R*,4R*)-3-(Naphthalen-2-ylmethoxy)-piperidin-4-yl]biphenyl-4-yl}-amine hydrochloride

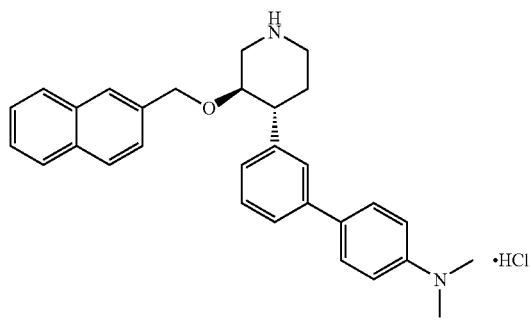 [SMILES: CN(C)c1ccc(-c2cccc([C@H]3CCNC[C@@H]3OCc3ccc4ccccc4c3)c2)cc1 ; Cl]

The title compound is prepared analogously as described in Example 13 using 4-(N,N-dimethylamino)phenylboronic acid: MS 437.7 [M+H]⁺; $R_f$ 0.25 (DCM/MeOH 9:1).

EXAMPLE 24

3'-[(3R*,4R*)-3-(Naphthalen-2-ylmethoxy)-piperidin-4-yl]-biphenyl-3-carboxylic acid hydrochloride

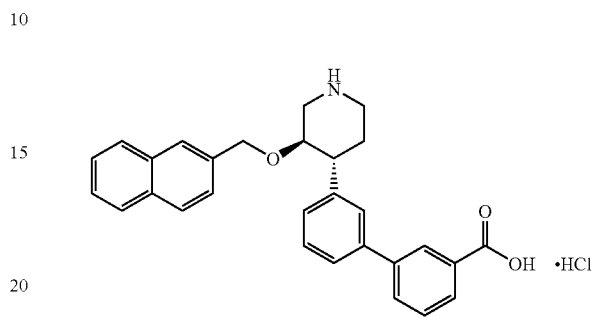

A stirred mixture of (3R*,4R*)-4-(3-bromo-phenyl)-3-(naphthalen-2-ylmethoxy)-piperidine-1-carboxylic acid t-butyl ester (300 mg, 0.6 mmol), 3-ethoxycarbonylphenyl boronic acid (136.8 mg, 0.71 mmol), dimethoxyethane (3 mL), H₂O (1 mL), tetrakis-(triphenylphosphin)-palladium (46.5 mg, 0.04 mmol) and Na₂CO₃ (96 mg, 0.91 mmol) is heated at reflux under argon for 16 h. The mixture is cooled to RT, dimethoxyethane is removed in vacuo and the residue is diluted with aqueous 2N Na₂CO₃ solution containing a few mL of concentrated NH₄OH. The aqueous layer is extracted three times with CH₂Cl₂. The combined organic extracts are dried (Na₂SO₄) and evaporated in vacuo. Flash chromatography of the dark residue (SiO₂, hexane/ethyl acetate) affords (3R*,4R*)-4-(3'-ethoxycarbonyl-biphenyl-3-yl)-3-(naphthalen-2-ylmethoxy)-piperidine-1-carboxylic acid t-butyl ester as a yellowish resin. The ester (138.7 mg, 0.245 mmol) is dissolved in MeOH (1 mL) and THF (1 mL), treated with aqueous NaOH (2 M, 0.5 mL, 1 mmol) and the mixture is stirred for 14 h at RT. The solvents are removed in vacuo, the residue is diluted with H₂O and the pH adjusted to 5 by the addition of 1N HCl. The aqueous phase is extracted twice with ethyl acetate. The combined organic extracts are dried (Na₂SO₄) and evaporated in vacuo to afford (3R*,4R*)-4-(3'-carboxy-biphenyl-3-yl)-3-(naphthalen-2-ylmethoxy)-piperidine-1-carboxylic acid t-butyl ester as a white amorphous solid. A mixture of this acid (110.1 mg, 0.20 mmol) and HCl (5M in 2-propanol, 2 mL, 10 mmol) is stirred for 1 h at RT. The reaction mixture is evaporated in vacuo and the residue purified using preparative HPLC (H₂O/CH₃CN). The combined pure fractions are treated with solid K₂CO₃ and CH₃CN is removed in vacuo. The aqueous layer is extracted twice with CH₂Cl₂. The combined organic extracts are dried (Na₂SO₄) and evaporated in vacuo. The residue is stirred with HCl (5M in 2-propanol, 1 mL, 5 mmol) for 2 h at RT. Evaporation of the solvent affords 3'-[(3R*,4R*)-3-(naphthalen-2-ylmethoxy)-piperidin-4-yl]-biphenyl-3-carboxylic acid hydrochloride as a white solid: MS 438.6 [M+H]⁺; retention time 5.23 min (HPLC, Nucleosil C18; 5→100% CH₃CN in H₂O within 8 min).

EXAMPLE 25

3'-[(3R*,4R*)-3-(Naphthalen-2-ylmethoxy)-piperidin-4-yl]-biphenyl-4-carboxylic acid methylamide hydrochloride

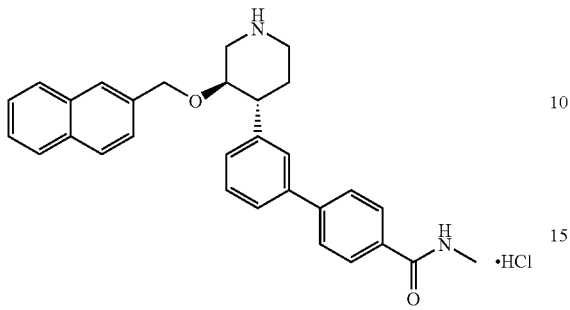

A stirred mixture of (3R*,4R*)-4-(3-bromo-phenyl)-3-(naphthalen-2-ylmethoxy)-piperidine-1-carboxylic acid t-butyl ester (173.8 mg, 0.35 mmol), 4-ethoxycarbonylphenyl boronic acid (135.8 mg, 0.70 mmol), dimethoxyethane (4.5 mL), H$_2$O (1.5 mL), tetrakis-(triphenylphosphin)-palladium (46.2 mg, 0.04 mmol) and Na$_2$CO$_3$ (111.3 mg, 1.05 mmol) is heated at reflux under argon for 14 h. The mixture is cooled to RT, dimethoxyethane is removed in vacuo and the residue is diluted with aqueous 2N Na$_2$CO$_3$ solution containing a few mL of concentrated NH$_4$OH. The aqueous layer is extracted three times with CH$_2$Cl$_2$. The combined organic extracts are dried (Na$_2$SO$_4$) and evaporated in vacuo. Flash chromatography of the dark residue (SiO$_2$, hexane/ethyl acetate) affords (3R*,4R*)-4-(4'-ethoxycarbonyl-biphenyl-3-yl)-3-(naphthalen-2-ylmethoxy)-piperidine-1-carboxylic acid t-butyl ester as a yellowish resin. A stirred mixture of this ester and CH$_3$NH$_2$ (8M in EtOH, 5 mL, 40 mmol) is heated at 80° C. for 24 h in a pressure bottle. The reaction mixture is evaporated in vacuo to afford (3R*,4R*)-4-(4'-methylcarbamoyl-biphenyl-3-yl)-3-(naphthalen-2-ylmethoxy)-piperidine-1-carboxylic acid t-butyl ester as a viscous yellowish oil. A mixture of this compound (62.4 mg, 0.11 mmol) and HCl (5M in 2-propanol, 3 mL, 15 mmol) is stirred for 1 h at RT. The reaction mixture is evaporated in vacuo to afford 3'-[(3R*,4R*)-3-(naphthalen-2-ylmethoxy)-piperidin-4-yl]-biphenyl-4-carboxylic acid methylamide hydrochloride as a white solid. MS 451.7 [M+H]$^+$; R$_f$ 0.13 (DCM/MeOH 9:1).

EXAMPLE 26

4-{3-[(3R*,4R*)-3-(Naphthalen-2-ylmethoxy)-piperidin-4-yl]-phenyl}-pyridine hydrochloride

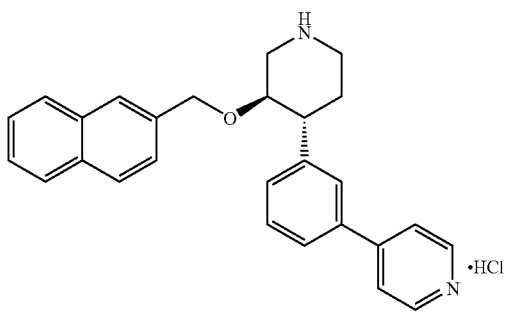 [SMILES: c1cc(-c2ccncc2)cc([C@H]2CCNC[C@@H]2OCc2ccc3ccccc3c2)c1 ; Cl]

The title compound is prepared analogously as described in Example 13 using pyridine-4-boronic acid: MS 395.6 [M+H]$^+$; retention time 3.76 min (HPLC, Nucleosil C18; 5→100% CH$_3$CN in H$_2$O within 8 min).

EXAMPLE 27

(3R*,4R*)-3-(Naphthalen-2-ylmethoxy)-4-(3-thiophen-3-yl-phenyl)-piperidine hydrochloride

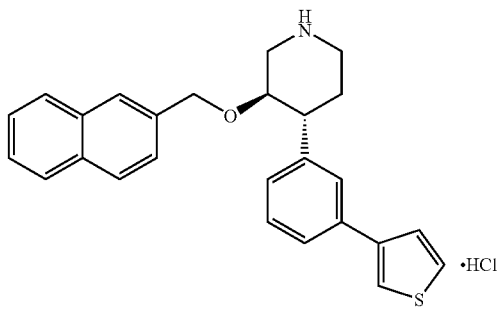 [SMILES: c1cc(-c2ccsc2)cc([C@H]2CCNC[C@@H]2OCc2ccc3ccccc3c2)c1 ; Cl]

The title compound is prepared analogously as described in Example 13 using thiophene-3-boronic acid: MS 400.6 [M+H]$^+$; retention time 5.88 min (HPLC, Nucleosil C18; 5→100% CH$_3$CN in H$_2$O within 8 min).

EXAMPLE 28

3-{3-[(3R*,4R*)-3-(Naphthalen-2-ylmethoxy)-piperidin-4-yl]-phenyl}-pyridine hydrochloride

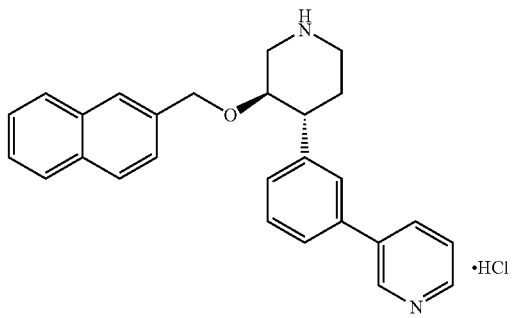 [SMILES: c1cncc(-c2cccc([C@H]3CCNC[C@@H]3OCc3ccc4ccccc4c3)c2)c1 ; Cl]

The title compound is prepared analogously as described in Example 13 using pyridine-3-boronic acid: MS 395.5 [M+H]$^+$; retention time 3.87 min (HPLC, Nucleosil C18; 5→100% CH$_3$CN in H$_2$O within 8 min).

EXAMPLE 29

2-{3-[(3R*,4R*)-3-(Naphthalen-2-ylmethoxy)-piperidin-4-yl]-phenyl}-1H-indole hydrochloride

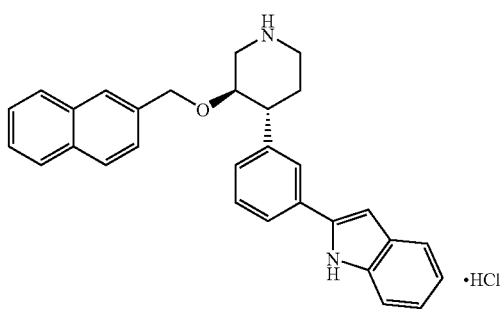 [SMILES: c1cc(-c2cc3ccccc3[nH]2)cc([C@H]2CCNC[C@@H]2OCc2ccc3ccccc3c2)c1 ; Cl]

The title compound is prepared analogously as described in Example 13 using 1-(t-butoxycarbonyl)indole-2-boronic acid: MS 433.6 [M+H]+; retention time 6.09 min (HPLC, Nucleosil C18; 5→100% CH₃CN in H₂O within 8 min).

EXAMPLE 30

5-{3-[(3R*,4R*)-3-(Naphthalen-2-ylmethoxy)-piperidin-4-yl]-phenyl}-pyrimidine hydrochloride

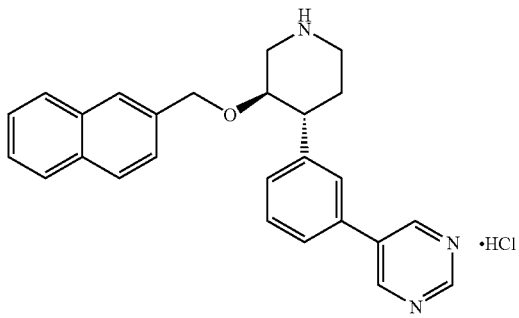 [SMILES: c1cc(-c2cncnc2)cc([C@H]2CCNC[C@@H]2OCc2ccc3ccccc3c2)c1 ; Cl]

The title compound is prepared analogously as described in Example 13 using pyrimidine-5-boronic acid: MS 396.6 [M+H]+; retention time 4.47 min (HPLC, Nucleosil C18; 5→100% CH₃CN in H₂O within 8 min).

EXAMPLE 31

(3R,4R)-4-Biphenyl-3-yl-3-[2-(3-methoxy-propoxy)-4-methyl-benzyloxy]-piperidine

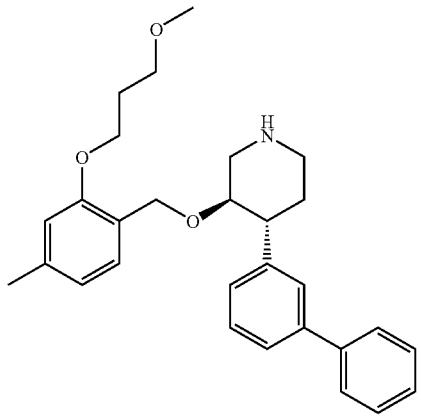 [SMILES: COCCCOc1cc(C)ccc1CO[C@H]1CNCC[C@@H]1c1cccc(-c2ccccc2)c1]

A. 4-Biphenyl-3-yl-3,6,dihydro-2H-pyridine-1-carboxylic acid ethyl ester

The title compound is prepared analogously as described for the title A compound in Example 1.

B. (3S,4S)-4-Biphenyl-3-yl-3,4-dihydroxy-piperidine-1-carboxylic acid ethyl ester To a stirred solution of AD-mix-α (20.13 g, 18.3 mmol) in tBuOH (120 mL) and H₂O (120 mL) is added methansulfonamid (1.92 g, 19.6 mmol). The reaction mixture is cooled to 0° C. followed by addition of a solution of the title A compound, 4-biphenyl-3-yl-3,6,dihydro-2H-pyridine-1-carboxylic acid ethyl ester (4.1 g, 13.07 mmol) in tBuOH (10 mL) and H₂O (10 mL). The reaction is stirred at 0° C. for 30 min and allowed to stir over the week end at room temperature. To the reaction mixture is added 18 g of Na₂SO₃ followed by stirring for 1 h before the addition of methylene chloride. The layers are separated and the aqueous one extracted 3 times with methylene chloride. The combined organic extracts are washed with a 2N sodium hydroxide solution, dried over anhydrous sodium sulfate and concentrated under reduced pressure. Purification by flash column chromatography (CH₂Cl₂/MeOH: 95/5) affords the desired product of (3S,4S)-4-biphenyl-3-yl-3,4-dihydroxy-piperidine-1-carboxylic acid ethyl ester. TLC, Rf (CH₂Cl₂/MeOH: 95/5)=0.69. MS 339.9 [M−H]. Rt (HPLC, Nucleosil C18, 10:90-100:0 CH₃CN/H₂O+0.1% TFA within 5 min, then 100% CH₃CN+0.1% TFA): 5.26 min.

C. (3R,4R)-4-Biphenyl-3-yl-3-hydroxy-piperidine-1-carboxylic acid ethyl ester

To a vigorously stirred solution of the title B compound, (3S,4S)-4-biphenyl-3-yl-3,4-dihydroxy-piperidine-1-carboxylic acid ethyl ester (4.2 g, 12.05 mmol) in EtOH (250 mL) is added 6.5 g Raney-Nickel. The stirred suspension is heated to reflux for 4 h, then allowed to cool to room temperature, filtered over a celite pad and rinsed with EtOH. The solvent is removed under reduced pressure and purification by flash column chromatography (hexane/EtOAc 4/1 to ½) affords the desired product: (3R,4R)-4-Biphenyl-3-yl-3-hydroxy-piperidine-1-carboxylic acid ethyl ester. TLC, Rf (Hexane/EtOAc 2/1)=0.65. MS 326.1 [M+H]. Rt (HPLC, Nucleosil C18, 10:90-100:0 CH₃CN/H₂O+0.1% TFA within 5 min, then 100% CH₃CN+0.1% TFA): 5.62 min.

D. (3R,4R)-4-Biphenyl-3-yl-3-[2-(3-methoxy-propoxy)-4-methyl-benzyloxy]-piperidine-1-carboxylic acid ethyl ester A suspension of the title C compound, (3R,4R)-4-biphenyl-3-yl-3-hydroxy-piperidine-1-carboxylic acid ethyl ester (150 mg, 0.45 mmol) and sodium hydride (60% dispersion in mineral oil, 30 mg, 0.68 mmol) in 10 mL of dry DMF is stirred for 10 min at 60° C. under argon. After cooling to room temperature, 1-bromomethyl-2-(3-methoxy-propoxy)-4-methyl-benzene (252 mg, 0.9 mmol) is added and the mixture further stirred for 3 h at 60° C. After addition of H₂O, the aqueous layer is extracted twice with ethyl acetate and the combined organic extracts are dried over anhydrous sodium sulfate and concentrated under reduced pressure. The residue is purified by preparative HPLC (Macherey-Nagel 250/4 nucleosil 100-10 C18 column, 20:80 CH₃CN+0.1% TFA over 11 min, then 100% CH₃CN+0.1% TFA for 5.5 min, 40 ml/min). To the combined fractions containing the desired product is added 1M aqueous sodium carbonate solution and the acetonitrile is removed under reduced pressure. The resulting aqueous suspension is extracted twice with ethyl acetate. The combined organic layers are dried over anhydrous sodium sulfate, filtered and concentrated under reduced pressure to afford the title compound. MS 535.2 [M+18]; Rt (HPLC, Nucleosil C18, 10:90-100:0 CH₃CN/H₂O+0.1% TFA within 5 min, then 100% CH₃CN+0.1% TFA): 7.29 min.

E. (3R,4R)-4-Biphenyl-3-yl-3-[2-(3-methoxy-propoxy)-4-methyl-benzyloxy]-piperidine To a solution of the title D compound, (3R,4R)-4-biphenyl-3-yl-3-[2-(3-methoxy-propoxy)-4-methyl-benzyloxy]-piperidine-1-carboxylic acid ethyl ester (50 mg, 0.95 mmol) in 2 mL of absolute ethanol is added 2 mL of a 10% aqueous solution of sodium hydroxide. The resulting mixture is heated at 170° C. for 45 min in a microwave. The solvent is removed under reduced pressure and the resulting aqueous suspension is extracted twice with methylene chloride. The combined organic layers are dried over anhydrous sodium sulfate, filtered and concentrated under reduced pressure. The residue is purified by preparative HPLC (Macherey-Nagel 250/4 nucleosil 100-10 C18 column, 20:80 CH$_3$CN+0.1% TFA over 11 min, then 100% CH$_3$CN+0.1% TFA for 5.5 min, 40 mL/min). To the combined fractions containing the desired product is added 1M aqueous sodium carbonate solution and the acetonitrile is removed under reduced pressure. The resulting aqueous suspension is extracted twice with ethyl acetate. The combined organic layers are dried over anhydrous sodium sulfate, filtered and concentrated under reduced pressure affording the title compound as a colorless oil. A solution of the compound in acetonitrile is lyophilized. MS 446.1 [M+H]. Rt (HPLC, Nucleosil C18, 10:90-100:0 CH$_3$CN/H$_2$O+0.1% TFA within 5 min, then 100% CH$_3$CN+0.1% TFA): 5.48 min.

EXAMPLE 32

(3R,4R)-4-Biphenyl-3-yl-3-[2-(3-methoxy-propoxy)-benzyloxy]-piperidine trifluoroacetic acid

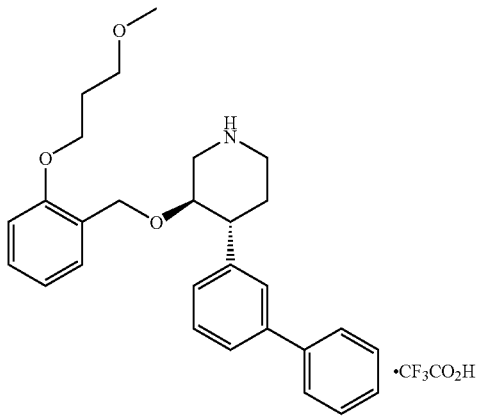

The title compound is prepared analogously as described in Example 31, except that the product is purified by HPLC, and the combined fractions containing the desired product are concentrated under reduced pressure and a solution of the compound in acetonitrile is lyophilized to afford (3R,4R)-4-biphenyl-3-yl-3-[2-(3-methoxy-propoxy)-benzyloxy]-piperidine trifluoroacetic acid: MS 432.2 [M+H]; Rt (HPLC, Nucleosil C18, 10:90-100:0 CH$_3$CN/H$_2$O+0.1% TFA within 5 min, then 100% CH$_3$CN+0.1% TFA): 5.53 min.

EXAMPLE 33

(3R,4R)-4-Biphenyl-3-yl-3-[4-methoxy-3-(-3-methoxy-propoxy)-benzyloxy]-piperidine

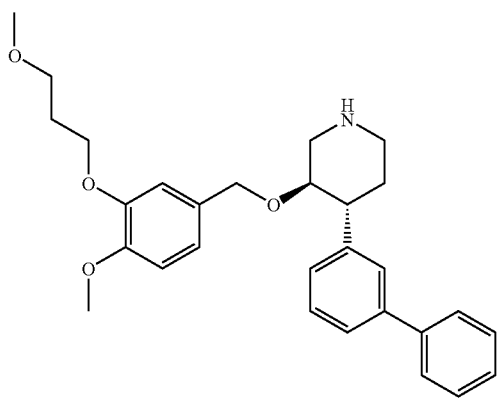 [SMILES: COCCCOc1cc(CO[C@H]2CNCC[C@@H]2c2cccc(-c3ccccc3)c2)ccc1OC]

The title compound Is prepared analogously as described in Example 31. MS 462.0 [M+H]. Rt (HPLC, Nucleosil C18, 10:90-100:0 CH$_3$CN/H$_2$O+0.1% TFA within 5 min, then 100% CH$_3$CN+0.1% TFA): 5.13 min.

EXAMPLE 34

(3R,4R)-4-Biphenyl-3-yl-3-[3-(4-methoxy-butyl)-benzyloxy]-piperidine

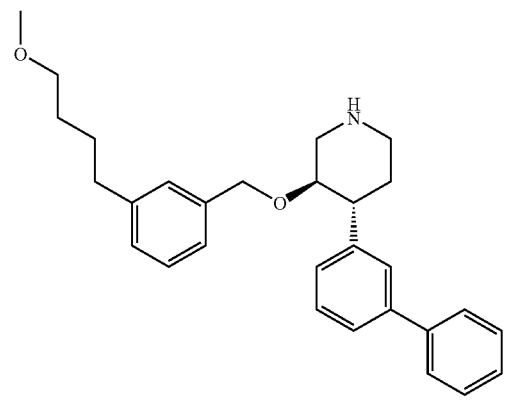 [SMILES: COCCCCc1cccc(CO[C@H]2CNCC[C@@H]2c2cccc(-c3ccccc3)c2)c1]

The title compound is prepared analogously as described in Example 31. MS 429.9 [M+H]. Rt (HPLC, Nucleosil C18, 10:90-100:0 CH$_3$CN/H$_2$O+0.1% TFA within 5 min, then 100% CH$_3$CN+0.1% TFA): 5.64 min.

EXAMPLE 35

(3R,4R)-4-Biphenyl-3-yl-3-[3-(3-methoxy-propyl)-benzyloxy]-piperidine

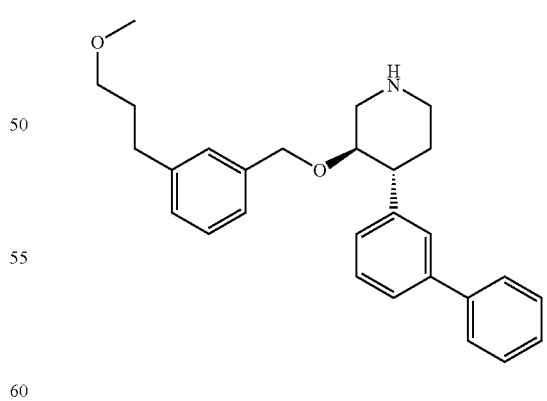

The title compound is prepared analogously as described in Example 31. MS 416.1 [M+H]. Rt (HPLC, Nucleosil C18, 10:90-100:0 CH$_3$CN/H$_2$O+0.1% TFA within 5 min, then 100% CH$_3$CN+0.1% TFA): 5.44 min.

EXAMPLE 36

(3R,4R)-4-Biphenyl-3-yl-3-[3-(2-methoxy-ethyl)-benzyloxy]-piperidine

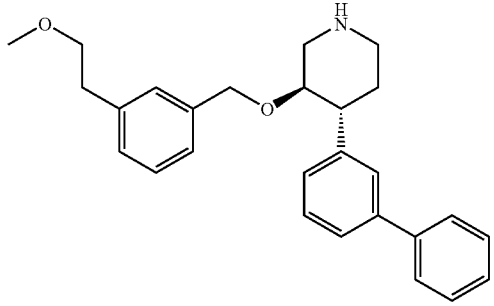 [SMILES: COCCc1cccc(CO[C@H]2CNCC[C@@H]2c2cccc(-c3ccccc3)c2)c1]

The title compound is prepared analogously as described in Example 31. MS 402.0 [M+H]. Rt (HPLC, Nucleosil C18, 10:90-100:0 CH$_3$CN/H$_2$O+0.1% TFA within 5 min, then 100% CH$_3$CN+0.1% TFA): 5.24 min.

EXAMPLE 37

(3R,4R)-4-Biphenyl-3-yl-3-[3-(3-methoxy-propyl)-4-methyl-benzyloxy]-piperidine

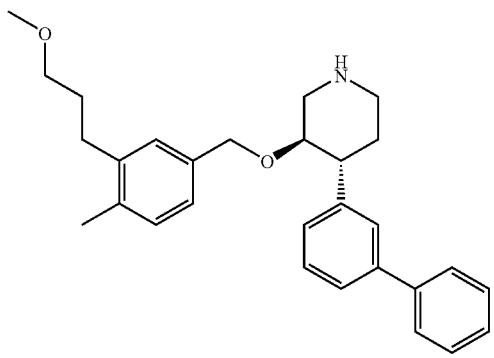 [SMILES: COCCCc1cc(CO[C@H]2CNCC[C@@H]2c2cccc(-c3ccccc3)c2)ccc1C]

The title compound is prepared analogously as described in Example 31. MS 429.9 [M+H]. Rt (HPLC, Nucleosil C18, 10:90-100:0 CH$_3$CN/H$_2$O+0.1% TFA within 5 min, then 100% CH$_3$CN+0.1% TFA) 5.56 min.

EXAMPLE 38

(3R,4R)-4-Biphenyl-3-yl-3-[3-(4-methoxy-butyl)-4-methyl-benzyloxy]-piperidine

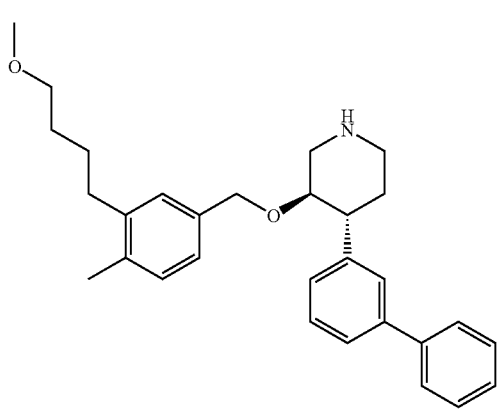 [SMILES: COCCCCc1cc(CO[C@H]2CNCC[C@@H]2c2cccc(-c3ccccc3)c2)ccc1C]

The title compound is prepared analogously as described in Example 31. MS 444.0 [M+H]. Rt (HPLC, Nucleosil C18, 10:90-100:0 CH$_3$CN/H$_2$O+0.1% TFA within 5 min, then 100% CH$_3$CN+0.1% TFA): 5.65 min.

EXAMPLE 39

(3R,4R)-4-Biphenyl-3-yl-3-[2-(3-methoxy-propyl)-benzyloxy]-piperidine trifluoroacetic acid

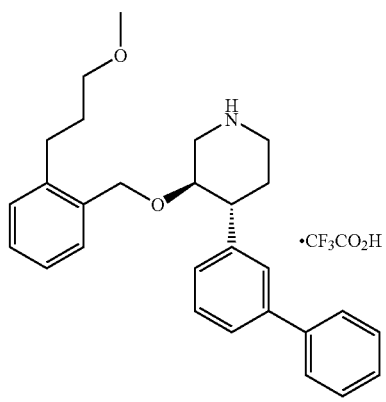 [SMILES: COCCCc1ccccc1CO[C@H]1CNCC[C@@H]1c1cccc(-c2ccccc2)c1 ; "·CF3CO2H"]

The title compound is prepared analogously as described in Example 31, except that the product is purified by HPLC, and the combined fractions containing the desired product are concentrated under reduced pressure and a solution of the compound in acetonitrile is lyophilized to afford (3R,4R)-4-biphenyl-3-yl-3-[2-(3-methoxy-propyl)-benzyloxy]-piperidine trifluoroacetic acid: MS 416.2 [M+H]; Rt (HPLC, Nucleosil C18, 10:90-100:0 CH$_3$CN/H$_2$O+0.1% TFA within 5 min, then 100% CH$_3$CN+0.1% TFA): 5.56 min.

EXAMPLE 40

(3R,4R)-3-(1-Benzyl-cyclopropylmethyloxy)-4-biphenyl-3-yl-piperidine trifloroacetic acid

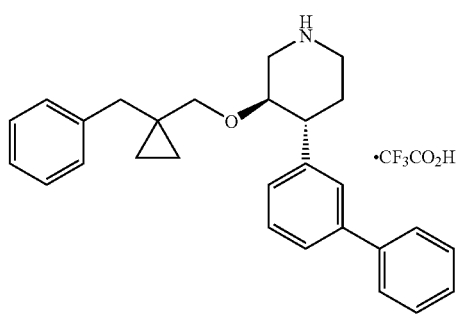 [SMILES: c1ccc(CC2(CO[C@H]3CNCC[C@@H]3c3cccc(-c4ccccc4)c3)CC2)cc1 ; "·CF3CO2H"]

The title compound is prepared analogously as described in Example 31, except that the product is purified by HPLC, and the combined fractions containing the desired product are concentrated under reduced pressure and a solution of the compound in acetonitrile is lyophilized to afford: (3R,4R)-3-(1-benzyl-cyclopropylmethyloxy)-4-biphenyl-3-yl-piperidine trifloroacetic acid: MS 397.8 [M+H]; Rt (HPLC, Nucleosil C18, 10:90-100:0 CH$_3$CN/H$_2$O+0.1% TFA within 5 min, then 100% CH$_3$CN+0.1% TFA): 5.67 min.

EXAMPLE 41

(3R,4R)-4-Biphenyl-3-yl-3-{1-[2-(3-methoxy-propyl)-benzyl]-cyclopropylmethoxy}-piperidine hydrochloride

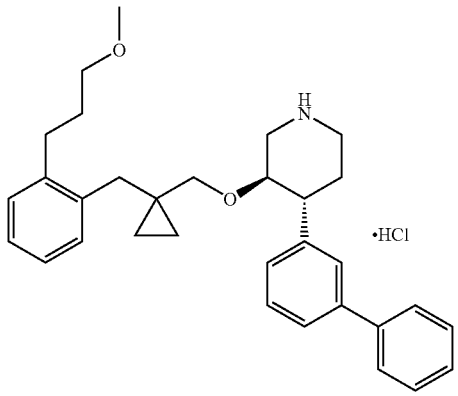 [SMILES: COCCCc1ccccc1CC1(CO[C@H]2CNCC[C@@H]2c2cccc(-c3ccccc3)c2)CC1 ; Cl]

The free base of the title compound is prepared analogously as described in Example 31. The compound is then treated with HCl (4M in 1,4-dioxane, 2 eq.) and stirred for 30 min at RT. Evaporation of the solvent in vacuum yields (3R, 4R)-4-biphenyl-3-yl-3-{1-[2-(3-methoxy-propyl)-benzyl]-cyclopropylmethoxy}-piperidine hydrochloride: MS 470.1 [M+H]; Rt (HPLC, Nucleosil C18, 10:90-100:0 $CH_3CN/H_2O$+0.1% TFA within 5 min, then 100% $CH_3CN$+0.1% TFA): 5.88 min.

EXAMPLE 42

1-Bromomethyl-2-(3-methoxy-propoxy)-4-methyl-benzene

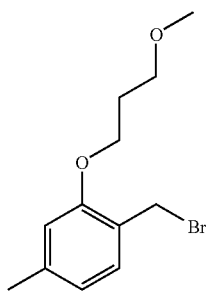

A. Toluene-4-sulfonic acid 3-methoxy-propyl ester

A solution of 3-methoxy-1-propanol (6 g, 65.24 mmol), triethylamine (27.5 mL, 195.7 mmol) and tosylchloride (18.85 g, 97.9 mmol) in methylene chloride (50 mL) is stirred for 3 h at room temperature under nitrogen. The mixture is poured into $H_2O$, and the aqueous layer extracted twice with methylene chloride. The combined organic extracts are dried over anhydrous sodium sulfate and concentrated under reduced pressure. The residue is purified by flash column chromatography on silica gel (hexane/EtOAc 4/1) to afford the title compound as an orange oil: MS 261.9 [M+18]; Rt (HPLC, Nucleosil C18, 10:90-100:0 $CH_3CN/H_2O$+0.1% TFA within 5 min, then 100% $CH_3CN$+0.1% TFA): 5.21 min.

B. 2-(3-Methoxy-propoxy)-4-methyl-benzaldehyde

A solution of 2-hydroxy-4-methylbenzaldehyde (3 g, 21.6 mmol), potassium carbonate (14.9 g, 107.8 mmol) and the title A compound, toluene-4-sulfonic acid 3-methoxy-propyl ester (8.07 g, 32.4 mmol) in DMF (50 mL) is stirred at 50° C. for 3 h. The solvent is concentrated under reduced pressure, $H_2O$ is added, and the aqueous layer extracted twice with ethyl acetate. The combined organic extracts are dried over anhydrous sodium sulfate and concentrated under reduced pressure to afford the title compound together with 30% of remaining tosylate: Rt (HPLC, Nucleosil C18, 10:90-100:0 $CH_3CN/H_2O$+0.1% TFA within 5 min, then 100% $CH_3CN$+ 0.1% TFA): 5.25, 5.39 min. The mixture is further used as is in the next step.

C. [2-(3-Methoxy-propoxy)-4-methyl-phenyl]-methanol

To a solution of the title B compound, 2-(3-methoxy-propoxy)-4-methyl-benzaldehyde (3.7 g, 17.41 mmol) in 30 mL of methanol is added portion wise sodium borohydride (1.03 g, 26.12 mmol). The reaction mixture is stirred for 30 min at room temperature. Sodium borohydride (1.03 g, 26.12 mmol) is added and the mixture further stirred overnight to complete the reaction. After addition of $H_2O$, the aqueous layer is extracted twice with ethyl acetate. The combined organic extracts are dried over anhydrous sodium sulfate and concentrated under reduced pressure. The residue is purified by flash column chromatography on silica gel (hexane/EtOAc 4/1 to 1/2) to afford the title compound as a colorless oil: TLC, Rf (hexane/AcOEt 2/1)=0.2. Rt (HPLC, Nucleosil C18, 10:90-100:0 $CH_3CN/H_2O$+0.1% TFA within 5 min, then 100% $CH_3CN$+0.1% TFA): 4.88 min.

D. 1-Bromomethyl-2-(3-methoxy-propoxy)-benzene

To a solution of the title C compound, [2-(3-methoxy-propoxy)-4-methyl-phenyl]-methanol (300 mg, 1.4 mmol) in 5 mL of chloroform is added trimethylbromosilane (0.28 mL, 2.1 mmol), with stiffing at room temperature. After 2 h the solvent is evaporated off and the crude residue is purified by flash column chromatography on silica gel (hexane/EtOAc 1/1) to afford the title compound as a colorless oil (0.4 g). Rt (HPLC, Nucleosil C18, 10:90-100:0 $CH_3CN/H_2O$+0.1% TFA within 5 min, then 100% $CH_3CN$+0.1% TFA): 4.70 min.

EXAMPLE 43

1-Bromomethyl-2-(3-methoxy-propoxy)-benzene

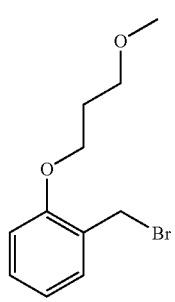

A. 2-(3-Methoxy-propoxy)-benzaldehyde

A solution of 2-hydroxy-benzaldehyde (1.5 g, 12.16 mmol), potassium carbonate (8.4 g, 60.8 mmol) and toluene-4-sulfonic acid 3-methoxy-propyl ester (14.85 g, 60.8 mmol) in DMF (30 mL) is stirred at 50° C. for 3 h. The solvent is concentrated under reduced pressure, $H_2O$ is added, and the aqueous layer extracted twice with ethyl acetate. The combined organic extracts are dried over anhydrous sodium sulfate and concentrated under reduced pressure. The residue is purified by flash column chromatography on silica gel (hexane/EtOAc 4/1 to 1/2) to afford the title compound together with 50% of remaining tosylate: MS 195.0 [M+H]. Rt (HPLC, Nucleosil C18, 10:90-100:0 $CH_3CN/H_2O$+0.1% TFA within 5 min, then 100% $CH_3CN$+0.1% TFA): 5.08 min. The mixture is further used as is in the next step.

B. [2-(3-Methoxy-propoxy)-phenyl]-methanol

The title compound is prepared analogously as described for the title C compound in Example 42 TLC, Rf (hexane/AcOEt 2/1)=0.46. Rt (HPLC, Nucleosil C18, 10:90-100:0 $CH_3CN/H_2O$+0.1% TFA within 5 min, then 100% $CH_3CN$+0.1% TFA): 4.58 min.

C. 1-Bromomethyl-2-(3-methoxy-propoxy)-benzene

The title compound is prepared analogously as described for the title D compound in Example 42 MS 275.7, 277.8 [M+18]. Rt (HPLC, Nucleosil C18, 10:90-100:0 $CH_3CN/H_2O$+0.1% TFA within 5 min, then 100% $CH_3CN$+0.1% TFA): 5.84 min.

EXAMPLE 44

4-Bromomethyl-1-methoxy-2-(3-methoxy-propoxy)-benzene

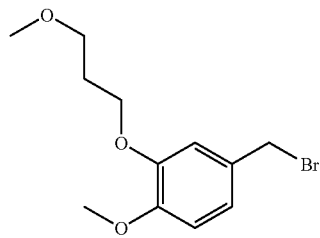 [SMILES: COCCCOc1cc(CBr)ccc1OC]

A. 4-Methoxy-3-(3-methoxy-propoxy)-benzaldehyde

To a solution of 3-hydroxy-4-methoxy-benzaldehyde (3.04 g, 20 mmol) and 3-methoxy-propanol (1.80 g, 20 mmol) in THF (150 mL) is added triphenylphosphine (5.24 g, 20 mmol) at room temperature under nitrogen atmosphere. To the stirring mixture is added diethyl azodicarboxylate (3.11 mL, 20 mmol) over 10 min at room temperature, and the resulting solution is further stirred over 20 h. THF is removed under reduced pressure and the remaining residue is purified by flash chromatography on silica gel (hexane/EtOAc 2/1) to afford the title compound: TLC, Rf (hexane/EtOAc 2/1)=0.2.

B. [4-Methoxy-3-(3-methoxy-propoxy)-phenyl]-methanol

To a solution of the title A compound, 4-methoxy-3-(3-methoxy-propoxy)-benzaldehyde (2.02 g, 8.9 mmol) in 60 mL of THF is added portion wise sodium borohydride (0.74 g, 18.73 mmol) at 0° C. The reaction mixture is stirred for 6 hours at room temperature. After addition of $H_2O$, the aqueous layer is extracted twice with ethyl acetate. The combined organic extracts are dried over anhydrous sodium sulfate and concentrated under reduced pressure to afford the title compound as a colorless oil: TLC, Rf (hexane/AcOEt 1/1)=0.34.

C. 4-Bromomethyl-1-methoxy-2-(3-methoxy-propoxy)-benzene

The title compound is prepared analogously as described for the title D compound in Example 42 TLC, Rf (hexane/AcOEt 1/1)=0.57. Rt (HPLC, Nucleosil C18, 10:90-100:0 $CH_3CN/H_2O$+0.1% TFA within 5 min, then 100% $CH_3CN$+0.1% TFA): 4.89 min.

EXAMPLE 45

1-Bromomethyl-3-(4-methoxy-butyl)-benzene

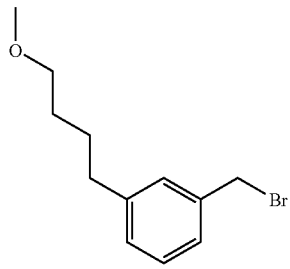

A. (3-Methoxy-propyl)-triphenyl-phosphonium bromide

A solution of $PPh_3$ (42.8 g, 163.2 mmol) and 1-bromo-3-methoxypropane (25 g, 163.3 mmol) in toluene (70 mL) is heated at 150° C. in an autoclave for 44 h. After completion of the reaction, the mixture is filtered and the precipitate washed with toluene and dried under high vacuum for 4 h affording the title compound as a white powder. Rt (HPLC, Nucleosil C18, 10:90-100:0 $CH_3CN/H_2O$+0.1% TFA within 5 min, then 100% $CH_3CN$+0.1% TFA): 5.06 min.

B. 1-Bromo-3-(4-methoxy-but-1-enyl)-benzene

To a stirred solution of NaHMDS (9.02 g, 49.2 mmol) in THF (50 mL) under nitrogen atmosphere is added drop wise at 0° C. a THF solution (50 mL) of the title A compound, (3-methoxy-propyl)-triphenyl-phosphonium bromide (20.4 g, 49.2 mmol). The resulting mixture is stirred for 1 h at 0° C. before the addition of a THF solution (50 mL) of m-bromobenzaldehyde (7 g, 37.8 mmol). The reaction mixture is further stirred for 2 h at room temperature and poured into a saturated $NH_4Cl$ aqueous solution, the aqueous layer is extracted twice with EtOAc. The combined organic extracts are dried over anhydrous magnesium sulfate and concentrated under reduced pressure. The residue is taken up into ether and the triphenylphosphine oxide precipitate is filtered off through a pad of celite. The filtrate is concentrate and the residual material purified by flash column chromatography on silica gel (hexane/EtOAc 95/5) to afford the title compound (as a mixture Z and E stereoisomers) as a yellow oil: Rt (HPLC, Nucleosil C18, 10:90-100:0 $CH_3CN/H_2O$+0.1% TFA within 5 min, then 100% $CH_3CN$+0.1% TFA): 6.30 min.

C. 1-Bromo-3-(4-methoxy-butyl)-benzene

A suspension of the title B compound, 1-bromo-3-(4-methoxy-but-1-enyl)-benzene (1.8 g, 7.46 mmol) and Pd/c 5% (0.36 g) in THF (20 mL) is shaken under an hydrogen atmosphere. After completion of the reaction, the mixture is filtered through a pad of celite, the solvent is evaporated under reduced pressure and the residue purified by flash chromatography on silica gel (hexane/EtOAc 98/2) to give the title compound as a yellow oil: MS 260.1, 261.9 [M+18]. Rt (HPLC, Nucleosil C18, 10:90-100:0 $CH_3CN/H_2O$+0.1% TFA within 5 min, then 100% $CH_3CN$+0.1% TFA): 6.45 min.

D. 3-(4-Methoxy-butyl)-benzaldehyde

To a stirred solution of the title C compound, 1-bromo-3-(4-methoxy-butyl)-benzene (11 g, 45.24 mmol) in 200 mL of THF is added drop wise n-butyl lithium (31.1 mL, 49.76 mmol, 1.6 M solution in hexane) over 30 min at −72° C. The reaction mixture is further stirred 5 min at −72° C. before the addition of a THF solution (50 mL) of DMF (7.67 mL, 99.52 mmol) over 45 min. The reaction mixture is further stirred for 15 min at −72° C., 1 h at room and poured into aqueous 2 M HCl solution. The aqueous layer is extracted twice with ether and the combined organic extracts are dried over anhydrous sodium sulfate and concentrated under reduced pressure. The residue is purified by flash column chromatography on silica gel (hexane/EtOAc 9/1) to afford the title compound as a yellow oil: MS 210.0 [M+18]; Rt (HPLC, Nucleosil C18, 10:90-100:0 $CH_3CN/H_2O$+0.1% TFA within 5 min, then 100% $CH_3CN$+0.1% TFA): 5.35 min.

E. [3-(4-Methoxy-butyl)-phenyl]-methanol

To a solution of the title D compound, 3-(4-methoxy-butyl)-benzaldehyde (0.1 g, 0.52 mmol) and MeOH (0.063 mL, 1.56 mmol) in 2 mL of THF is added portion wise sodium borohydride (20 mg, 0.52 mmol). The reaction mixture is stirred for 1 hour at room and poured into aqueous 1M HCl. The aqueous layer is extracted twice with ethyl acetate and the combined organic extracts are dried over anhydrous sodium sulfate and concentrated under reduced pressure. The residue is purified by flash column chromatography on silica gel (hexane/EtOAc 3/1) to afford the title compound as a colorless oil: TLC, Rf (hexane/AcOEt 2/1)=0.34. MS 212.1 [M+18].

F. 1-Bromomethyl-3-(4-methoxy-butyl)-benzene

The title compound is prepared analogously as described for the title D compound in Example 42 TLC, Rf (hexane/AcOEt 1/1)=0.8. MS 273.9, 276.0 [M+18]. Rt (HPLC, Nucleosil C18, 10:90-100:0 $CH_3CN/H_2O$+0.1% TFA within 5 min, then 100% $CH_3CN$+0.1% TFA): 6.10 min.

EXAMPLE 46

1-Bromomethyl-3-(3-methoxy-propyl)-benzene

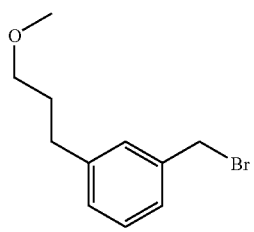

A. (2-Methoxy-ethyl)-triphenyl-phosphonium bromide

The title compound is prepared analogously as described for the title C compound in Example 45: Rt (HPLC, Nucleosil C18, 10:90-100:0 $CH_3CN/H_2O$+0.1% TFA within 5 min, then 100% $CH_3CN$+0.1% TFA): 5.09 min.

B. 1-Bromo-3-(3-methoxy-propenyl)-benzene

The title compound is prepared analogously as described for the title B compound in Example 45: Rt (HPLC, Nucleosil C18, 10:90-100:0 $CH_3CN/H_2O$+0.1% TFA within 5 min, then 100% $CH_3CN$+0.1% TFA): 5.97 min.

C. 1-Bromo-3-(3-methoxy-propyl)-benzene

The title compound is prepared analogously as described for the title C compound in Example 45: MS 226.9, 228.9 [M+H].

D. 3-(3-Methoxy-propyl)-benzaldehyde

The title compound is prepared analogously as described for the title D compound in Example 45: TLC, Rf (hexane/AcOEt 5/1)=0.37. MS 195.9 [M+18].

E. [3-(3-Methoxy-propyl)-phenyl]-methanol

The title compound is prepared analogously as described for the title E compound in Example 45: MS 198 [M+18]; TLC, Rf (hexane/AcOEt 2/1)=0.33.

F. 1-Bromomethyl-3-(3-methoxy-propyl)-benzene

The title compound is prepared analogously as described for the title F compound in Example 45: TLC, Rf (hexane/AcOEt 1/1)=0.85; MS 261.9, 262.8 [M+18]; Rt (HPLC, Nucleosil C18, 10:90-100:0 $CH_3CN/H_2O$+0.1% TFA within 5 min, then 100% $CH_3CN$+0.1% TFA): 5.85 min.

EXAMPLE 47

1-bromomethyl-3-(2-methoxy-ethyl)-benzene

A. Methoxymethyl-triphenyl-phosphonium bromide

The title compound is prepared analogously as described for the title A compound in Example 45 Rt (HPLC, Nucleosil C18, 10:90-100:0 $CH_3CN/H_2O$+0.1% TFA within 5 min, then 100% $CH_3CN$+0.1% TFA): 4.83 min.

B. 1-Bromo-3-(2-methoxy-vinyl)-benzene

The title compound is prepared analogously as described for the title B compound in Example 45: TLC, Rf (hexane/AcOEt 9/1)=0.65. Rt (HPLC, Nucleosil C18, 10:90-100:0 CH$_3$CN/H$_2$O+0.1% TFA within 5 min, then 100% CH$_3$CN+0.1% TFA): 6.01 and 6.09 min.

C. 1-Bromo-3-(2-methoxy-ethyl)-benzene

The title compound is prepared analogously as described for the title C compound in Example 45: TLC, Rf (hexane/AcOEt 9/1)=0.6. Rt (HPLC, Nucleosil C18, 10:90-100:0 CH$_3$CN/H$_2$O+0.1% TFA within 5 min, then 100% CH$_3$CN+0.1% TFA): 5.75 min.

D. 3-(2-Methoxy-ethyl)-benzaldehyde

The title compound is prepared analogously as described for the title D compound in Example 45: TLC, Rf (hexane/AcOEt 5/1)=0.37. MS 182.1 [M+18].

E. [3-(2-Methoxy-ethyl)-phenyl]-methanol

The title compound is prepared analogously as described for the title E compound in Example 45: MS 183.9 [M+18]. TLC, Rf (hexane/AcOEt 2/1)=0.22.

F. 1-Bromomethyl-3-(2-methoxy-ethyl)-benzene

The title compound is prepared analogously as described for the title F compound in Example 45: MS 246.0, 247.8 [M+18]; Rt (HPLC, Nucleosil C18, 10:90-100:0 CH$_3$CN/H$_2$O+0.1% TFA within 5 min, then 100% CH$_3$CN+0.1% TFA): 5.52 min.

EXAMPLE 48

4-Bromomethyl-2-(3-methoxy-propyl)-1-methyl-benzene

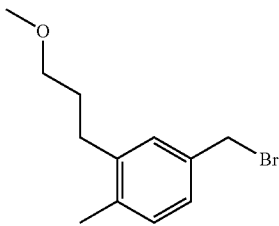

A. 5-Bromo-2-methyl-benzaldehyde

To a stirred solution of aluminum chloride (57.93 g, 434.46 mmol) in methylene chloride (200 mL) is added at 0° C. over 45 min o-methylbenzaldehyde (30 g, 249.69 mmol). To the resulting brown mixture is further added a methylene chloride solution (200 mL) of bromine (12.71 mL, 249.69 mmol) over 3 h and the reaction mixture is allowed to reach room temperature overnight. The reaction mixture is then poured into ice (600 g) and the aqueous layer is extracted twice with methylene chloride. The combined organic extracts are washed with a saturated aqueous solution of NaHCO$_3$, dried over anhydrous magnesium sulfate and concentrated under reduced pressure. The residue is taken up into hexane and the precipitate is filtered, washed with hexane (this protocol is repeated twice) and dried under high vacuum to afford the title compound as a mixture of two regioisomers: 5-bromo-2-methyl-benzaldehyde and 3-bromo-2-methyl-benzaldehyde in a 80/20 ratio: MS 197.0, 199.0 [M−H]. Rt (HPLC, Nucleosil C18, 10:90-100:0 CH$_3$CN/H$_2$O+0.1% TFA within 5 min, then 100% CH$_3$CN+0.1% TFA): 5.52 min.

B. 4-Bromo-2-(3-methoxy-propenyl)-1-methyl-benzene

The title compound is prepared analogously as described for the title B compound in Example 45 using (2-methoxy-ethyl)-triphenyl-phosphonium bromide (prepared in Example 46) and the title A compound, 5-bromo-2-methyl-benzaldehyde (containing 20% of 3-bromo-2-methyl-benzaldehyde) (6 g, 30.14 mmol): TLC, Rf (hexane/AcOEt 9/1)=0.48. Rt (HPLC, Nucleosil C18, 10:90-100:0 CH$_3$CN/H$_2$O+0.1% TFA within 5 min, then 100% CH$_3$CN+0.1% TFA): 6.26, 6.34 min.

C. 4-Bromo-2-(3-methoxy-propyl)-1-methyl-benzene

The title compound is prepared analogously as described for the title C compound in Example 45: MS 243.0, 245.0 [M−H]. TLC, Rf (hexane/AcOEt 9/1)=0.63.

D. 3-(3-Methoxy-propyl)-4-methyl-benzaldehyde

The title compound is prepared analogously as described for the title D compound in Example 45: MS 192.9 [M+H], 210.0 [M+18].

E. [3-(3-Methoxy-propyl)-4-methyl-phenyl]-methanol

The title compound is prepared analogously as described for the title E compound in Example 45: TLC, Rf (hexane/AcOEt 2/1)=0.38; MS 212.2 [M+18].

F. 4-Bromomethyl-2-(3-methoxy-propyl)-1-methyl-benzene

The title compound is prepared analogously as described for the title F compound in Example 45: MS 273.9, 276 [M+18]. Rt (HPLC, Nucleosil C18, 10:90-100:0 CH$_3$CN/H$_2$O+0.1% TFA within 5 min, then 100% CH$_3$CN+0.1% TFA): 6.09 min.

EXAMPLE 49

4-Bromomethyl-2-(4-methoxy-butyl)-1-methyl-benzene

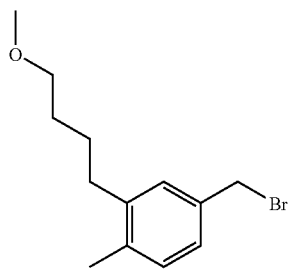

A. 4-Bromo-2-(4-methoxy-but-1-enyl)-1-methyl-benzene

The title compound is prepared analogously as described for the title B compound in Example 45 using (3-methoxy-propyl)-triphenyl-phosphonium bromide and 5-bromo-2-methyl-benzaldehyde (prepared in Example 48; containing 20% of 3-bromo-2-methyl-benzaldehyde): Rt (HPLC, Nucleosil C18, 10:90-100:0 $CH_3CN/H_2O$+0.1% TFA within 5 min, then 100% $CH_3CN$+0.1% TFA): 6.60 min.

B. 4-Bromo-2-(4-methoxy-butyl)-1-methyl-benzene

The title compound is prepared analogously as described for the title C compound in Example 45: Rt (HPLC, Nucleosil C18, 10:90-100:0 $CH_3CN/H_2O$+0.1% TFA within 5 min, then 100% $CH_3CN$+0.1% TFA): 6.72 min.

C. 3-(4-Methoxy-butyl)-4-methyl-benzaldehyde

The title compound is prepared analogously as described for the title D compound in Example 45: TLC, Rf (hexane/AcOEt 9/1)=0.5; MS 224.1 [M+18].

D. [3-(4-Methoxy-butyl)-4-methyl-phenyl]-methanol

The title compound is prepared analogously as described for the title E compound in Example 45: MS 225.9 [M+18]; TLC, Rf (hexane/AcOEt 2/1)=0.4. Rt (HPLC, Nucleosil C18, 10:90-100:0 $CH_3CN/H_2O$+0.1% TFA within 5 min, then 100% $CH_3CN$+0.1% TFA): 5.04 min.

E. 4-Bromomethyl-2-(4-methoxy-butyl)-1-methyl-benzene

The title compound is prepared analogously as described for the title F compound in Example 45: TLC, Rf (hexane/AcOEt 1/1)=0.85; MS 288.0, 289.8 [M+18]; Rt (HPLC, Nucleosil C18, 10:90-100:0 $CH_3CN/H_2O$+0.1% TFA within 5 min, then 100% $CH_3CN$+0.1% TFA): 6.35 min.

EXAMPLE 50

1-Bromomethyl-2-(3-methoxy-propyl)-benzene

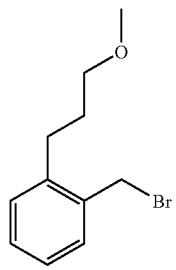

A. 3-(2-Hydroxymethyl-phenyl)-propan-1-ol (Malandra, J. L.; Trahanovski, W. S. *JOC* 1995, 60, 261-263)

In a solution of 1,2-dihydronaphtalene (6.5 g, 50 mmol) in methylene chloride (200 mL) ozone is bubbled at −75° C. until a blue color developed. Excess of ozone is then removed by bubbling nitrogen through the solution until the blue color has dissipated. The reaction mixture is allowed to reach room temperature and the solvent partially removed under vacuum. The resulting ozonide is dissolved in THF (50 mL) and this solution is added drop wise at 0° C. to a solution of $LiAlH_4$ (55 mL, 55 mmol, 1M in THF) in THF (125 mL). The reaction mixture is further stirred for 4 h at room temperature, and wet $Na_2SO_4$ is added to the reaction mixture until the evolution of $H_2$ ceased. The mixture is filtered off and the white solid washed with EtOAc. The filtrate is dried over anhydrous magnesium sulfate and concentrated under reduced pressure. The residue is purified by flash column chromatography on silica gel (hexane/EtOAc 4/1 to EtOAc/MeOH 95/5) to afford the title compound: TLC, Rf (AcOEt)=0.40. MS 183.9 [M+18].

B. [2-(3-Methoxy-propyl)-phenyl]-methanol

To a suspension of the title A compound, 3-(2-hydroxymethyl-phenyl)-propan-1-ol (14.9 g, 90 mmol) and proton-sponge (25 g, 1.3 eq.) in methylene chloride (500 mL) is added at 0° C. under nitrogen trimethyloxonium-tetrafluoroborate (17.3 g, 117 mmol). The reaction mixture is further stirred for 5 h at room temperature before filtration. The filtrate is poured into water and the aqueous layer extracted twice with methylene chloride. The combined organic extracts are dried over $Na_2SO_4$, filtered and concentrated under reduced pressure. The residue is purified by flash column chromatography on silica gel (hexane/EtOAc 7/3 to 1/1 and to AcOEt/MeOH 9/1) to afford the title compound: TLC, Rf (hexane/AcOEt 4/1)=0.57. MS 198.0 [M+18].

C. 1-Bromomethyl-2-(3-methoxy-propyl)-benzene

The title compound is prepared analogously as described for the title D compound in Example 42: TLC, Rf (hexane/AcOEt 95/5)=0.4. MS 259.8, 261.9 [M+18].

EXAMPLE 51

(1-Bromomethyl-cyclopropylmethyl)-benzene

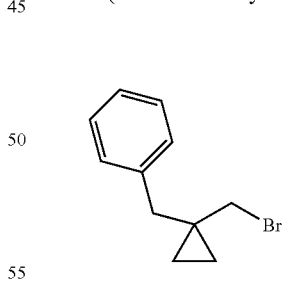

A. Cyclopropanecarboxylic acid tert-butyl ester

To a solution of tert-butanol (9.4 mL, 100 mmol) in 50 mL of anhydrous THF is added under nitrogen during several minutes n-butyl lithium (69 mL, 110 mmol, 1.6 M solution in hexane). After 30 min, the resulting solution is treated by the drop wise addition of a THF solution (40 mL) of cyclopropanecarbonyl chloride (10 mL, 110 mmol). The reaction mixture is further stirred at reflux for 1 h, cooled to 0° C. by an ice bath, and slowly hydrolyzed by the addition of water. The aqueous layer is extracted twice with ether and the combined organic extracts are dried over anhydrous sodium sulfate and concentrated under reduced pressure. The residue is purified by vacuum distillation (bp=70° C., 76 mmHg) to afford the title compound as a yellow oil.

B. 1-Benzyl-cyclopropanecarboxylic acid tert-butyl ester

To a stirring solution of LDA (11 mL, 22 mmol, 2 M in THF) in THF (40 mL) under nitrogen is added drop wise at −75° C. a THF solution (10 mL) of the title A compound, cyclopropanecarboxylic acid tert-butyl ester (2.85 g, 20 mmol). The resulting mixture is stirred for 5 h at −75° C. before the addition of a THF solution (10 mL) of benzylbromide (3.8 mL, 32 mmol). The reaction mixture is allowed to reach room temperature overnight and poured into a saturated $NH_4Cl$ aqueous solution. The aqueous layer is extracted twice with EtOAc and the combined organic extracts are dried over anhydrous magnesium sulfate and concentrated under reduced pressure. The residue is purified by flash column chromatography on silica gel (hexane/EtOAc 97/3) to afford the title compound: TLC, Rf (hexane/AcOEt 95/5)=0.47; MS 249.9 [M+18].

C. (1-Benzyl-cyclopropyl)-methanol

To a stirring solution of the title B compound, 1-benzyl-cyclopropanecarboxylic acid tert-butyl ester (0.232 g, 1 mmol) in THF (8 mL) under nitrogen is added drop wise at −50° C. $LiAlH_4$ (3 mL, 3 mmol, 1 m in THF). The resulting mixture is further stirred for 1 h at −50° C., then slowly allowed to reach room temperature and poured into a saturated $NaHCO_3$ aqueous solution. The aqueous layer is extracted twice with EtOAc. and the combined organic extracts are dried over anhydrous magnesium sulfate and concentrated under reduced pressure. The residue is purified by flash column chromatography on silica gel (hexane/EtOAc 4/1 to 1/1) to afford the title compound: TLC, Rf (hexane/AcOEt 1/1)=0.52. MS 180.0 [M+18]. Rt (HPLC, Nucleosil C18, 10:90-100:0 $CH_3CN/H_2O$+0.1% TFA within 5 min, then 100% $CH_3CN$+0.1% TFA): 4.95 min.

D. (1-Bromomethyl-cyclopropylmethyl)-benzene

To a solution of the title C compound, (1-benzyl-cyclopropyl)-methanol (0.8 g, 4.93 mmol), pyridine (994 uL, 12.3 mmol) and $CBr_4$ (1.8 g, 5.42 mmol) in methylene chloride (25 mL) is added triphenylphosphine (1.8 g, 6.9 mmol), with stirring at 0° C. After completion of the reaction, the mixture is poured into a saturated aqueous solution of $NaHCO_3$. The aqueous layer is extracted twice with methylene chloride and the combined organic extracts are dried over anhydrous magnesium sulfate and concentrated under reduced pressure. The residue is taken up into ether and the triphenylphosphine oxide precipitate is filtered off. The filtrate is concentrated under reduced pressure and purified by flash column chromatography on silica gel (hexane/EtOAc 9/1) to afford the title compound: TLC, Rf (hexane/AcOEt 99/1)=0.54. Rt (HPLC, Nucleosil C18, 10:90-100:0 $CH_3CN/H_2O$+0.1% TFA within 5 min, then 100% $CH_3CN$+0.1% TFA): 6.41 min.

EXAMPLE 52

1-(1-Bromomethyl-cyclopropylmethyl)-2-(3-methoxy-propyl)-benzene

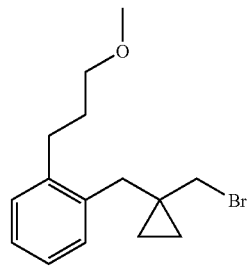 [SMILES: COCCCc1ccccc1CC1(CBr)CC1]

A. 1-[2-(3-Methoxy-propyl)-benzyl]-cyclopropanecarboxylic acid tert-butyl ester The title compound is prepared analogously as described for the title B compound in Example 51: TLC, Rf (hexane/AcOEt 95/5)=0.2. MS 322.2 [M+18].

B. {1-[2-(3-Methoxy-propyl)-benzyl]-cyclopropyl}-methanol

The title compound is prepared analogously as described for the title C compound in Example 51: TLC, Rf (hexane/AcOEt 1/1)=0.42.

C. 1-(1-Bromomethyl-cyclopropylmethyl)-2-(3-methoxy-propyl)-benzene

The title compound is prepared analogously as described for the title D compound in Example 51: TLC, Rf (hexane/AcOEt 95/5)=0.52.

What is claimed is:
1. A compound of the formula

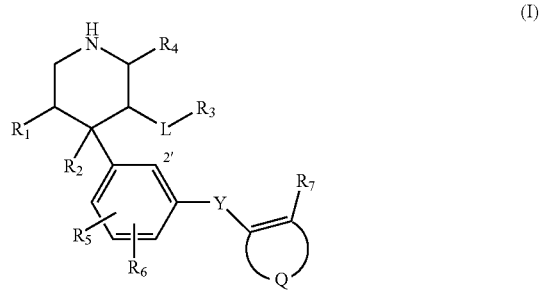

wherein
$R_1$ is —O—X; and
X is $—(CH_2)_m—(CR_9R_{10})_p—(CH_2)_n—Z—(CH_2)_q—W$
in which m is 1;
n and q are zero;
p is zero;
Z is a bond;
W is naphthyl;

$R_2$ is hydrogen;
L is a bond;
$R_3$ is hydrogen;
$R_4$ is hydrogen;
$R_5$ and $R_6$ are independently hydrogen, halogen, hydroxy, trifluoromethyl, optionally substituted lower alkyl, lower alkoxy or cycloalkyl; or
$R_5$ and $R_6$ combined together with the carbon atoms to which they are attached form a fused 5- to 6-membered aromatic or heteroaromatic ring provided that $R_5$ and $R_6$ are attached to carbon atoms adjacent to each other; or
$R_5$ and $R_6$ combined are alkylene which together with the carbon atoms to which they are attached form a fused 5- to 7-membered ring provided that $R_5$ and $R_6$ are attached to carbon atoms adjacent to each other; or
C—$R_5$ and C—$R_6$ may be replaced with nitrogen;
$R_7$ is hydrogen, halogen, hydroxy, trifluoromethyl, optionally substituted lower alkyl, lower alkoxy, cycloalkyl, alkanoyl, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, carboxy, alkoxycarbonyl, aryl, alkenyl, alkynyl, aralkoxy, heterocyclyl including indolyl, imidazolyl, furyl, thienyl, thiazolyl, pyrrolidyl, pyridyl, pyrimidyl, piperidyl, morpholinyl and tetrazolyl; or
$R_7$ and $R_6$ combined are O, $S(O)_{0-2}$, —$NR_{14}$—, —$(CH_2)_{1-2}$—, —O—$CH_2$—, —$CH_2$—O—, $S(O)_{0-2}$—$CH_2$—, —$CH_2$—$S(O)_{0-2}$—, —$CH_2$—$NR_{14}$—, —$S(O)_{0-2}$—$NR_{14}$— or —$NR_{14}$—$S(O)_{0-2}$— in which
$R_{14}$ is hydrogen or lower alkyl, provided $R_6$ is located at the 2' position; or
C—$R_7$ may be replaced with nitrogen;
Y is —$(CH_2)_r$—, in which
r is zero;
Q combined with the atoms to which it is attached form a 5- to 6-membered monocyclic aromatic or heteroaromatic ring; or
Q combined with the atoms to which it is attached form a 7- to 12-membered bicyclic aromatic or heterocyclic ring;
or a pharmaceutically acceptable salt thereof.

2. A compound according to claim 1 wherein
$R_1$ is —O—X; and
X is —$(CH_2)_m$—$(CR_9R_{10})_p$—$(CH_2)_n$—Z—$(CH_2)_q$—W in which
m is 1;
n is zero;
p is zero;
q is zero;
Z is a bond;
W is naphthyl;
$R_2$ is hydrogen;
L is a bond;
$R_3$ is hydrogen;
$R_4$ is hydrogen;
$R_5$ and $R_6$ are independently hydrogen, halogen, hydroxy, trifluoromethyl, optionally substituted lower alkyl, lower alkoxy or cycloalkyl; or
$R_5$ and $R_6$ combined together with the carbon atoms to which they are attached form a fused 5- to 6-membered aromatic or heteroaromatic ring provided that $R_5$ and $R_6$ are attached to carbon atoms adjacent to each other; or
$R_5$ and $R_6$ combined are alkylene which together with the carbon atoms to which they are attached form a fused 5- to 7-membered ring provided that $R_5$ and $R_6$ are attached to carbon atoms adjacent to each other; or
$R_7$ is hydrogen, halogen, hydroxy, trifluoromethyl, optionally substituted, lower alkyl, lower alkoxy or cycloalkyl; or
$R_7$ and $R_6$ combined are O, $S(O)_{0-2}$, —$NR_{14}$—, —$(CH_2)_{1-2}$—, —O—$CH_2$—, —$CH_2$—O—, —$S(O)_{0-2}$—$CH_2$—, —$CH_2$—$S(O)_{0-2}$—, —$CH_2$—$NR_{14}$—, —$S(O)_{0-2}$—$NR_{14}$— or —$NR_{14}$—$S(O)_{0-2}$— in which
$R_{14}$ is hydrogen or lower alkyl, provided $R_6$ is located at the 2' position;
Y is —$(CH_2)_r$— in which
r is zero;
Q combined with the carbon atoms to which it is attached form a 5- to 6-membered monocyclic aromatic or heteroaromatic ring; or
Q combined with the carbon atoms to which it is attached form a 9- to 10-membered bicyclic aromatic or heterocyclic ring;
or a pharmaceutically acceptable salt thereof.

3. A compound according to claim 2 of the formula

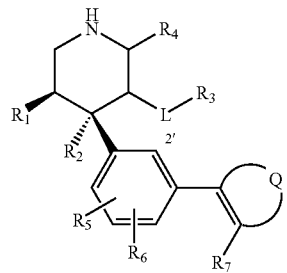

(IA)

wherein
$R_1$, $R_2$, L, $R_3$, $R_4$, $R_5$, $R_6$, $R_7$ and Q have meanings as defined in claim 2;
or a pharmaceutically acceptable salt thereof.

4. A compound according to claim 2 of the formula

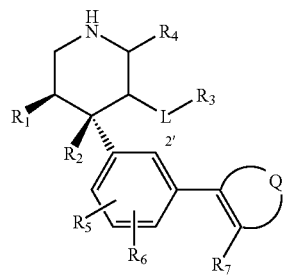

(IB)

wherein
$R_1$, $R_2$, L, $R_3$, $R_4$, $R_5$, $R_6$, $R_7$ and Q have meanings as defined in claim 2;
or a pharmaceutically acceptable salt thereof.

5. A compound according to claim 4 wherein
$R_1$ is —O—X; and
X is —$(CH_2)_m$—$(CR_9R_{10})_p$—$(CH_2)_n$—Z—W in which
m is 1;
n is zero;
p is zero;
Z is a bond;
W is naphthyl;
$R_2$ is hydrogen;

L is a bond;
R₃ is hydrogen;
R₄ is hydrogen;
R₅ and R₆ are independently hydrogen, halogen, hydroxy, trifluoromethyl, optionally substituted lower alkyl, lower alkoxy or cycloalkyl;
R₇ is hydrogen, halogen, hydroxy, trifluoromethyl, optionally substituted lower alkyl, lower alkoxy or cycloalkyl; or
R₇ and R₆ combined are O, S(O)$_{0\text{-}2}$, —NR₁₄—, —(CH₂)$_{1\text{-}2}$—, —O—CH₂—, —CH₂—O—, —S(O)$_{0\text{-}2}$—CH₂—, —CH₂—S(O)$_{0\text{-}2}$—, —CH₂—NR₁₄—, —S(O)$_{0\text{-}2}$—NR₁₄— or —NR₁₄—S(O)$_{0\text{-}2}$— in which
R₁₄ is hydrogen or lower alkyl, provided R₆ is located at the 2'-position;
Q combined with the atoms to which it is attached form a 5- to 6-membered monocyclic aromatic or heteroaromatic ring; or
Q combined with the atoms to which it is attached form a 9- to 10-membered bicyclic aromatic or heterocyclic ring;
or a pharmaceutically acceptable salt thereof.

6. A compound according to claim 5 wherein
Q combined with the carbon atoms to which it is attached form a pyridyl or pyrimidinyl ring;
or a pharmaceutically acceptable salt thereof.

7. A compound according to claim 5 wherein
Q combined with the carbon atoms to which it is attached form a thienyl, furyl, pyrrolyl or indolyl ring;
or a pharmaceutically acceptable salt thereof.

8. A compound according to claim 5 of the formula

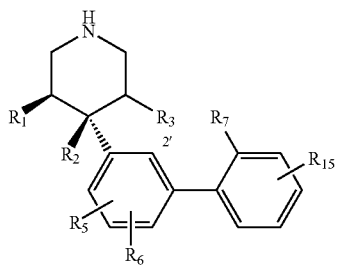

(IC)

wherein
R₁ is O—X; and
X is —(CH₂)$_m$—(CR₉R₁₀)$_p$—(CH₂)$_n$—Z—W in which
m is 1;
n and p are zero;
Z is a bond;
W is naphthyl;
R₂ is hydrogen;
R₃ is hydrogen;
R₅ and R₆ are independently hydrogen, halogen, hydroxy, trifluoromethyl, optionally substituted lower alkyl, lower alkoxy or cycloalkyl;
R₇ is hydrogen, halogen, hydroxy, trifluoromethyl, optionally substituted lower alkyl, lower alkoxy or cycloalkyl; or
R₇ and R₆ combined are O, S(O)$_{0\text{-}2}$, —NR₁₄—, —(CH₂)$_{1\text{-}2}$—, —O—CH₂—, —CH₂—O—, —S(O)$_{0\text{-}2}$—CH₂—, —CH₂—S(O)$_{0\text{-}2}$—, —NR₁₄—CH₂—, —CH₂—NR₁₄—, —S(O)$_{0\text{-}2}$—NR₁₄— or —NR₁₄—S(O)$_{0\text{-}2}$— in which
R₁₄ is hydrogen or lower alkyl, provided R₆ is located at the 2'-position;

R₁₅ is hydrogen, halogen, hydroxy, trifluoromethyl, optionally substituted lower alkyl, lower alkoxy or cycloalkyl;
or a pharmaceutically acceptable salt thereof.

9. A compound according to claim 8 wherein
R₁ is O—X; and
X is —(CH₂)$_m$—(CR₉R₁₀)$_p$—(CH₂)$_n$—Z—W in which
m is 1;
n and p are zero;
Z is a bond;
W is naphthyl;
R₃ is hydrogen;
R₅ is hydrogen, halogen, hydroxy, trifluoromethyl, optionally substituted lower alkyl, lower alkoxy or cycloalkyl;
R₆ is hydrogen;
R₇ is hydrogen;
R₁₅ is hydrogen, halogen, hydroxy, trifluoromethyl, optionally substituted lower alkyl, lower alkoxy or cycloalkyl;
or a pharmaceutically acceptable salt thereof.

10. A compound of the formula

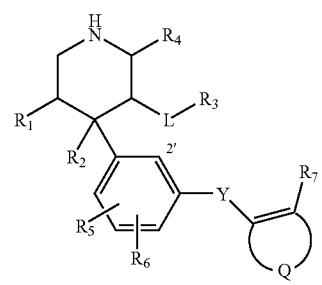

(I)

wherein
R₁ is —O—X; and
X is —(CH₂)$_m$—(CR₉R₁₀)$_p$—(CH₂)$_n$—Z—(CH₂)$_q$—W in which
m, n and q are independently zero or an integer from 1 to 5;
p is 1;
R₉ and R₁₀ combined are alkylene which together with the carbon atom to which they are attached form a 3- to 6-membered ring;
Z is a bond;
W is phenyl;
R₂ is hydrogen, halogen, cyano, hydroxy or lower alkoxy;
L is a bond;
R₃ is hydrogen; or
R₄ is hydrogen;
R₅ and R₆ are independently hydrogen, halogen, hydroxy, trifluoromethyl, optionally substituted lower alkyl, lower alkoxy or cycloalkyl; or
R₅ and R₆ combined together with the carbon atoms to which they are attached form a fused 5- to 6-membered aromatic or heteroaromatic ring provided that R₅ and R₆ are attached to carbon atoms adjacent to each other; or
R₅ and R₆ combined are alkylene which together with the carbon atoms to which they are attached form a fused 5- to 7-membered ring provided that R₅ and R₆ are attached to carbon atoms adjacent to each other; or
C—R₅ and C—R₆ may be replaced with nitrogen;
R₇ is hydrogen, halogen, hydroxy, trifluoromethyl, optionally substituted lower alkyl, lower alkoxy, cycloalkyl, alkanoyl, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, carboxy, alkoxycarbonyl, aryl, alkenyl, alkynyl, aralkoxy, heterocyclyl including indolyl, imidazolyl, furyl, thienyl, thiazolyl, pyrrolidyl, pyridyl, pyrimidyl, piperidyl, morpholinyl and tetrazolyl; or $R_7$ and $R_6$ combined are O, $S(O)_{0-2}$, $-NR_{14}-$, $-(CH_2)_{1-2}-$, $-O-CH_2-$, $-CH_2-O-$, $-S(O)_{0-2}-CH_2-$, $-CH_2-S(O)_{0-2}-$, $-NR_{14}-CH_2-$, $-CH_2-NR_{14}-$, $-S(O)_{0-2}-NR_{14}-$ or $-NR_{14}-S(O)_{0-2}-$ in which $R_{14}$ is hydrogen or lower alkyl, provided $R_6$ is located at the 2' position; or $C-R_7$ may be replaced with nitrogen;

Y is $-(CH_2)_r-$, in which
r is zero;

Q combined with the atoms to which it is attached form a 5- to 6-membered monocyclic aromatic or heteroaromatic ring; or Q combined with the atoms to which it is attached form a 7- to 12-membered bicyclic aromatic or heterocyclic ring; or a pharmaceutically acceptable salt thereof.

11. A pharmaceutical composition comprising a therapeutically effective amount of a compound of claim 1 in combination with one or more pharmaceutically acceptable carriers.

\* \* \* \* \*